US007592171B2

(12) United States Patent
Campos Gómez et al.

(10) Patent No.: US 7,592,171 B2
(45) Date of Patent: Sep. 22, 2009

(54) VIBRIO CHOLERAE WITH IMPROVED BIOLOGICAL SAFETY FEATURES IN FREEZE DRIED FORM

(75) Inventors: Javier Campos Gómez, Santa Clara (CU); Tomas Marcelino Moreira Hernandez, Habana (CU); Boris Luis Rodriguez Gonzalez, Habana (CU); Karen Marrero Dominguez, Habana (CU); Eriel Martinez Gutierrez, Habana (CU); Talena Yamile Ledon Perez, Habana (CU); Yussuan Silva Larrañaga, Habana (CU); Edith Suzarte Portal, Habana (CU); Herminia de la Caridad Delgado Rodriguez, Habana (CU); Caridad Urra Villavicencio, Habana (CU); Rafael Alfredo Fando Calzada, Habana (CU)

(73) Assignee: Centro Nacional de Investigaciones Cientificas (CNIC), Havana (CU)

( * ) Notice: Subject to any disclaimer, the term of this patent is extended or adjusted under 35 U.S.C. 154(b) by 396 days.

(21) Appl. No.: 10/546,410

(22) PCT Filed: Feb. 19, 2004

(86) PCT No.: PCT/CU2004/000002

§ 371 (c)(1),
(2), (4) Date: Jul. 3, 2006

(87) PCT Pub. No.: WO2004/073736

PCT Pub. Date: Sep. 2, 2004

(65) Prior Publication Data

US 2007/0071775 A1 Mar. 29, 2007

(30) Foreign Application Priority Data

Feb. 20, 2003 (CU) ................................ 2003-0039
Apr. 17, 2003 (CU) ................................ 2003-0084

(51) Int. Cl.
*C12N 1/04* (2006.01)
*C12N 1/20* (2006.01)
*A61K 39/106* (2006.01)

(52) U.S. Cl. .................. 435/252.1; 435/260; 424/261.1

(58) Field of Classification Search ....................... None
See application file for complete search history.

(56) References Cited

FOREIGN PATENT DOCUMENTS

WO WO 00/24430 * 5/2000

OTHER PUBLICATIONS

Campos et al (Journal of Bacteriology 185:7231-7240, 2003).*

* cited by examiner

*Primary Examiner*—Mary E Mosher
(74) *Attorney, Agent, or Firm*—Lackenbach Siegel, LLP

(57) ABSTRACT

The present invention discloses new live attenuated strains for oral immunization against cholera that are provided in freeze dried formulations for long term storage and administration to humans. These strains combine the two most important properties of live attenuated cholera vaccine candidates. One such property is being well tolerated by people ingesting them. This was achieved by virtue of mutations already described in the art. The second property is having enhanced environmental safety due to the absence of VGJΦ DNA in their genomes and also due to null mutations in the mshA gene or other spontaneous mutations conducive to the lack of MSHA type IV fimbria on the bacterial surface. This was done envisioning that VGJΦ is a filamentous phage able to recombine with CTXΦ and disseminate the cholera toxin genes. This VGJΦ phage as well as the VGJΦ-CTXΦ recombinants uses the MSHA fibers as receptor. Being devoid of MSHA fimbria the vaccine candidates are protected from acquiring CTXΦ from the recombinant hybrid VGJΦ-CTXΦ. Being devoid of VGJΦ, the vaccine candidates are impaired in the dissemination of CTXΦ, via VGJΦ.

3 Claims, 4 Drawing Sheets

Corte y reunión

| | |
|---|---|
| *att*-CTXϕ | ttccacatcCTTAGTGCGTATTATGTggcgcggca |
| *att*-VGJϕ | aggctgtttCTTACTTCGCATTATGTcggcctatg |
| *att*-CTX-VGJϕ | ttccacatcCTTAGTGCGTATTATGTcggcttatg |
| *att*-VGJ-CTXϕ | aggctgtttCTTACTTCGCATTATGTggcgcggca |

SEQUENCE LISTING

<160> NUMBER OF SEQ ID NOS: 1

<210> SEQ ID NO 1
<211> LENGTH: 7542
<212> TYPE: DNA
<213> ORGANISM: Filamentous phage of Vibrio cholerae
<220> FEATURE:
<221> NAME/KEY: ORF359 CDS
<222> LOCATION: (1)..(1077)
<223> OTHER INFORMATION: Similar to the replication protein, pII, from other filamentous phages
<220> FEATURE:
<221> NAME/KEY: ORF112 CDS
<222> LOCATION: (1085)..(1420)
<223> OTHER INFORMATION: Hypothetic Protein
<220> FEATURE:
<221> NAME/KEY: ORF81 CDS
<222> LOCATION: (1433)..(1675)
<223> OTHER INFORMATION: Hypothetic Protein
<220> FEATURE:
<221> NAME/KEY: ORF44 CDS
<222> LOCATION: (1690)..(1821)
<223> OTHER INFORMATION: Similar to the major protein from the Capsid, pVIII, from other filamentous phages
<220> FEATURE:
<221> NAME/KEY: ORF29 CDS
<222> LOCATION: (1839)..(1925)
<223> OTHER INFORMATION: Hypothetic Protein
<220> FEATURE:
<221> NAME/KEY: ORF493 CDS
<222> LOCATION: (1954)..(3432)
<223> OTHER INFORMATION: Similar to a minor protein from the Capsid, pIII, from other filamentous phages
<220> FEATURE:
<221> NAME/KEY: ORF80 CDS
<222> LOCATION: (3510)..(3749)
<223> OTHER INFORMATION: Hypothetic Protein
<220> FEATURE:
<221> NAME/KEY: ORF384 CDS
<222> LOCATION: (3755)..(4906)
<223> OTHER INFORMATION: Similar to a protein of the assembly, pI, from other filamentous phages
<220> FEATURE:
<221> NAME/KEY: ORF104 CDS
<222> LOCATION: (5232)..(5543)
<223> OTHER INFORMATION: Similar to a protein of the assembly, pI, from other filamentous phages
<220> FEATURE:
<221> NAME/KEY: ORF67 CDS
<222> LOCATION: (7328)..(7528)

-continued

<223> OTHER INFORMATION: Hypothetic protein
<220> FEATURE:
<221> NAME/KEY: ORF136 CDS
<222> LOCATION: (6105)..(6112)
<223> OTHER INFORMATION: Complementary chain
Putative transcriptional regulator 1
<220> FEATURE:
<221> NAME/KEY: ORF154 CDS
<222> LOCATION: (6439)..(6900)
<223> OTHER INFORMATION: Complementary chain
Putative transcriptional regulator 1
<220> FEATURE:
<221> NAME/KEY: ORF58 CDS
<222> LOCATION: (6439)..(6900)
<223> OTHER INFORMATION: Complementary chain
Hypothetic protein

<400> SEQUENCE: 1
atgatacggt tcgccctgtc aaagttgacc acttggcttt tactttcgcc tatgcggact 60
tgcgccactt ggacaaaagc aacgaccaag actttatcaa tctacagatg cccgtttatc 120
acgagccaaa gacccgaacc aaggaacaag gcgcggtgtg ctctaccttg gaacaaatcg 180
agcatcatat ggaagcgcac cgaaacaaag tgtccaagat gctctttcat cgctttgatt 240
tgttcatgtc caaaatcatg gctttcgtta tcgcctatgc gtggtcgtgg ccttcatggt 300
tacaacgatt ctatggtcat tctcgatatg accggacaag ttgagtgtgg ccttgtcgga 360
attggcggaa acaacgatac cgtttttgtc caaatcaacg gcacggggtg caccaaactt 420
ttcgaccgta tcgactctaa gaagcttcat tggtggctcg ctcaggttct tggcattact 480
cgcttagttc gtctcgactt ggccgtggac gattacaccg gaaacttcga cgccaagtat 540
gcagagaaat gtttttatga gggagcattt cgcactgctc cacgggggca aggtccctca 600
atggttcctc ataaacgcat tacagaaaac ggcgctttga tggaagaagc aacgattgtc 660
ggctctcgtt cctcggcgat ttactggcgt atctacaaca aaaagcttga gcaaaaaatt 720
actgaccctg acctgatttg gtatcgaaac gaggttgagc tgaaaaagtg cgacatcgag 780
cttttagcca atcctgccgc ctcttttgcg ggtatctgcc ctttcgcggc ctctatcgag 840
tgtacgcctc cggttaagtt ctctcgcaac aaaaaggctc aaggtcttga atttatggct 900
cgcatcgcat gggttcgccg tcaatgtggc gtggcgttag cggaagttat cgccatgacg 960
caaggcgatt taggcgaagc attcgggatg cttatccctc acaaacatag acgccctgac 1020
tttgaattgc tcggcgttcc tgattcatac acacaactga aaaacacact atggagttaa 1080
ggtaatggct aacatcactg gcatcgtcat caaaacattt cctaaatcgg gtaccacgat 1140
tgcagagctg aacgttcttc gccctgttga aaccgtcaac gttgagaagt ttgctcaata 1200
cggtttgggg ctaaacacgg atattccttt caataagcag ccgctgcgta tcgaacctac 1260
ttacgccaag cgtttgattg aaacacgcgc ttttgttcct aaccgtgaat atgacattcg 1320
ctttggtagt aaccctgacg acccattgga agtcgttgct gttgagctca tccccaagga 1380
tgacgacctt aaaaaatact ttactgaaac acttaaaaag taaggaagtt ttatgcctgt 1440
gtgcgctctc ccaaatagtc agggattcct agcggttact gacaagccac tgaatgaatg 1500
tgacggcggt tatgttgctt tcactattca ggattacgac tacttgatga gctacacacg 1560
cataacccca accgatgccg gaacggcctt tagcttcggt tttatggctg tattcgctct 1620
cggttattta tatacctatg ccgtttatat cggtaaaaaa ctcatcaacc tcttataagg 1680
agatacatca tggctgatat ctttggcgca attgattttg caggtgtcgc tgctcttgtt 1740
actgctgctg gtgttgccat cattggcatt actatggctt tcaaaggcat ctcacttggc 1800

-continued

```
aaacgcgctg ttaacaaagc ctaatcggta actgaactat gcttattgcc ctgcatgata   1860
ttcagttaat tattttcgcg ttgctgggtg gcatgtcggg ttttatagct gctctcaact   1920
tccgataaca aaggggctaa cgccccttt tttatggtta tgtttatgcg caaattttt     1980
attatctctc ttgtcattag cttatatttc accgttcttc ctgcttttgc tgcttatcag   2040
ttacctttg accaaacaaa gactttctca actgttcagg ccgccgctga gtattatgtc    2100
aatttacttg gtggtacttc atgcaaggct gacggtaaca ggtttaaaat ttacagagtt   2160
aaatctattg gcgacccctc ttttgttatt caacaagaaa cctatttaga caacaaatgt   2220
caggtctttt catcaaaggg tgatatcagc gttactctta ttgttgttga cgaccctacc   2280
acctgcgagg cttcaaaagg tcaaacagga aaagtcggtt ggaattctta cttctggggc   2340
tcggcaactc catcccgtta tatctgctct tctgcttatg gtggttgtgt tgccctcact   2400
ggtgaccatt tatgtattaa tattgaccct gaagcattga aaaatgaccc gtctctttat   2460
gattgcgatg ctctctatat cgttcaggat actccttgtt cccttctgg tgattatcca    2520
ttttgtaccg atgagaattg ctcttctttt cttcctgagc cgaatcctaa ccctaaccct   2580
gaaccagagc cggagccaga accccaacca gacccagaac acaatccctc tgacccgaca   2640
gcgccactcc ctggctctgg cggtgaagtc attaacccta ctgttcctcc taaaccaccg   2700
accgaggaaa cgcctaagcc tgacgtagaa acaccagacc ctacacctga ttcaaattct   2760
gacgttgttc aatctgttac cggaatgaat gaggatatga acgagttatt aactcgactc   2820
aattctgaca acaacaagca gcttgatgat gttaacaatc agctcttgca gctcaataca   2880
caatcacaac gtatcgttgc tcagattgcc aaacaggaaa aacaagatgc tgccatctac   2940
gaaaatacaa aggcacttat ccagaacctt aacaaagacg tgaccacggc cgttaacaaa   3000
accaccaatg ccgttaatgc tttgggctct aaagttgatg gcttatccga tgccgtcgat   3060
ggtcttggtg aagatgtatc agcaataaaa gatgtaatta ctaatgttga tacttctggg   3120
gctggtattt ctggcacttg tatagagtct gacacttgta cggggtttta tgaatctggt   3180
tatcctgatg gtatttcagg catattttca cagcattttg aaatcgtctc tgaaagtgtt   3240
actgataccg tcaaagactt tatgaaaatt gatttatctc acgctcaaag gccatcattt   3300
tctattccag ttctccactt tggaaatttc agctttgacg attatataaa ccttgattgg   3360
atatttggct ttgttcgtgt ttgcatgatg gtttcaactg ctttcctatg tcgtaaaata   3420
atattcggag gttaatatgg attgggtaat tgatttattt aaccaagctt atcgagtttc   3480
tttaccgctt attaatcacg cttattgata tgctaaagga tgttttcttg tggcttattg   3540
atggcgttct ttctgccgta aaccttttat tagagaaagc attatcactc atagaaccaa   3600
tggatgtttc ctcttacttg actggaatcc cttccggtgc tgcttgggtt attagcgcca   3660
ttggtatccc tcagtgtctt ggtatgatta tgtcagcaat cattgttcgt atcttattgc   3720
aactcgttcc attcactcgt ttaggttctt aattatgatt tatgcaattg ttggccgtcc   3780
tcgctctggt aagtcatacg agtctgttgt ttatcatatt attcccgccg ttaaatctgg   3840
ccgtaaagtc attacaaata ttcctttaaa tatggatatg tttgtaaagg ttttcggtga   3900
ttcggttaga gatttaatcc gcatcgtcga tgctaaattt aatgaatacg gttcaatgaa   3960
tagaccattt tcaaaggttg atgattatct tgatgactgg cgagatgata aaaaccgcgc   4020
tcctctttat gttattgatg aggctcatat ggttattcca actcgcctcg gtgatcaaag   4080
atacttgagt tctattcaat gcacggttca ttacggcatc gatattatta ttctcactca   4140
aaatttaaga aagattcatg ctgatattag agcaatgatt gagatgactt attactgtgc   4200
```

-continued taaaaatacc gcattcggca gtaaaaagac ttatacaaaa aaggttcgca tcggtgatac 4260
cagagaagac ttacacatag agcaacgcac ttacaaagaa cactatttcg gtttttatca 4320
atctcatact caaagcgcag gctctgtagt cgaagctcag gcattcgaca ttactcccat 4380
ttggaagcgc tggcctttct ggggctctct tgtctgcttc attatcgtta ttcttatact 4440
tgcttattat tttcagtcac gtaagtcaaa acacgctgaa gatgttcccc cagttcctga 4500
gcacagccaa cagactcctt catctgactc atccatttct caccctccta aacctcttca 4560
aaccataaag gctgctcctc tctctgagcc gctaagggat tttcagcttt acgtatctgg 4620
ccacgctaag cagatagcct ataaaaagat gtcattttct cgagagattg ataccaggct 4680
aaccttctat cacgtttaca ttagcgctta tcaggatgac aaattctctt tctctctcaa 4740
taacatagac ttagaaaaga tgggttatca atttgaggct ttaacggagt gcgtttatcg 4800
tattacttgg ggctctaatt ctcgtgtcat tacctgtatt gatgaaagcc gtttcaatca 4860
gcaaaaggcc gaaactgtat tcgaccacgt tcctaaactt gatatttgaa aagcgtttca 4920
gacttcaaac atcttgatta ttgaaacact tttcaaggaa tttgatttgt gtaacagatt 4980
tcatgacctt gattgctgta acatatatca agttacttga aatctgttac aggaatcaat 5040
tatgtcttat tgcaaatctt ctttcccaga ggctgatttt gctgtttatc aggagttcca 5100
aagaaagctt ggcccctaaa tataaatcta gaccagaggc cccctattag ccttgctcgc 5160
caatatatgg agaaataccc tgagtttcag cacattggcg gcattggtac acctctcgat 5220
gttattgacg aatgcttaga gcagattgct gcccttcaaa agcccaaaca cggaggaaac 5280
gcaagggcgc tgcccgtaag cctgcaccaa gtcaacttaa gcgcgttcct gttcctctca 5340
tcccaatcat tgaccgtatc atctcccaat ataaatcttg tgacttaaca tctttttcgc 5400
ttcttgcctt atatgattat ctagttactc aaagtttcag cctgtgcgag ggttctgttt 5460
ttaaaggtct ttttcttgat gatgttactt ttgaaccgtt agatgaccct gaacataatc 5520
ccccttcgat acaaaaaggt ttctgactac tttcttcaag ctggcctact tgatgacttt 5580
tacaattggg ctatctccaa cggccgcctt gctctttagc tttttaattt tctttattaa 5640
ctatccgcgc cttagtgcgc gacttttgag cttagctcga tgcccgcagg gactaggcca 5700
taacgttagc ctcaacacac tttgaacgta tgctactgca tatccgaaac actctaaggt 5760
tcgcggcggt tcgcttgatt ctaaagcgcg ccagtcagtc aagtgatcat caatactctt 5820
gcgccagaaa aaacaccctt cgccctgcca agccataaaa gatgtttcag caagcgcagt 5880
aggtagcagc attttctcgc cgtactatca acaacagggc gcggcgagtg tcgagcaagc 5940
catatttcat tcgttaagcg ttgcgctctg gaggggccca ctgggaggac acgggaggaa 6000
gcgccaaccc ccgagctgta tcacgggggt agattccacc atactccttg gtctcaccgt 6060
ataaatccct aaaaaaaatt agggctactg cctccctgct tttacttaat ccctttgatt 6120
ctagccatag ctctagcgta cttgagaagt ttagaacgtg tcattgcatc gtctggtgct 6180
tgtatttgca agatagcgat agcggctaat aactgctgtg gtgctaccct gtcacctgtt 6240
gggaatatca gtctcccccc ttccatccta aatccccacc actcatcacc gtaatacagc 6300
tcttttctgc tgtgccatct catcagcctc ttgcaaatcg gtggtatctt ctcccctgcg 6360
tcccattgct tgacctcgct cacagtttta aaacaaagtt tcgccgcttc ttcaacgctt 6420
aacccgcatt caaattcacg aaaaacaaaa ttctttgtca tttcgcttcg attcattgat 6480
aaaactccca aaagcggaag ttttataagc atttgaattt atagcaactt ttaccataag 6540

-continued

```
ccgacataat gcgaagtaag aaacagcctc gttaaactgg ctgattgaca ccgctagacc   6600

accgcaaagc attgatattg ttcttaatcc tagcccgttt tgcttttttg ctatgctttc   6660

ccaaatcgct ttgatgcgtg ggttttcgtt gcggtctgcg tgacatccta acagtgcgat   6720

ttcagggtca attcctgctg attcagctaa aaaaattgct tcttcatcag atatatacct   6780

aactccagtt ctcattttgc ttattttctg tggcgacaag ttcaagtcgt gtgcaatttg   6840

cttgtcttgt acgtagtttt ttgccttttt gtaggcgtct aacagttcat ttgcatacat   6900

atttatccct ccttttcttt tctatcatag cttgccaatc cccaatttgc gctatttaca   6960

atccccaaaa atgggactag aatcctcata aatcggaatt tgaccacctt gggcgctaga   7020

ccttaactct tccccttggt ggtctcccca accagttaag gcggttatca tggcaaattc   7080

agcaaagaaa caaaccctat cacaatctgt taacccattt gtgaccatcc agttaacttc   7140

tggcgctctt cctcgctttc ttgcttacgg cggctttaat tcggatggtt ctcagcgctc   7200

taagtaactt ctgtttctac tgatgcccca caaaatgccg cttcctactg caaacgcctt   7260

ttacccaagg ataagcgtaa ttggcctcta gctcagattt cctatcaggt taaataaggt   7320

cgctatcatg ggtgatttca tctactacga caacgaaccc aacatcggga tcaacgtgta   7380

tttcgtttgg gggcatcgtt tctttaaaaa ctggcctgag ttagagcaat accttgccat   7440

tcactatggc gctgacccat atcaactggt tgaaatcact aacgaaaact acaacgaatt   7500

gcttttaaag ggggtctttc atgccatgta agcaccctca cc                      7542
```

VIBRIO CHOLERAE WITH IMPROVED BIOLOGICAL SAFETY FEATURES IN FREEZE DRIED FORM

PRIOR RELATED APPLICATIONS

This application is a national stage application of PCT Patent Application PCT/CU2004/000002, filed Feb. 19, 2004, which claims priority to Cuban patent applications CU 2003-0039, filed Feb. 20, 2003, and CU 2003-0084, filed Apr. 17, 2003.

CROSS REFERENCE

This application is a national stage of PCT/CU2004/000002 filed Feb. 19, 2004 and is based upon Cuban Patent Applications No. 2003-0039, filed Feb. 20, 2003 and No. 2003-0084 filed Apr. 17, 2003 under the International Convention.

FIELD OF THE INVENTION

The field of invention is that of biotechnology, in particular, the obtainment of *Vibrio cholerae* live attenuated vaccine strains, more specifically, the introduction of defined mutations to prevent or limit the possibility of reacquisition and (or) the later dissemination of CTXΦ phage encoded genes by those live vaccine strains and a method to preserve them to be used as vaccines.

BACKGROUND OF THE INVENTION

First, Definitions:

During the description of the invention will be used a terminology whose meaning is listed bellow.

By CTXΦ virus is meant the particle of protein-coated DNA produced by certain *V. cholerae* strains, which is capable of transducing its DNA, comprising cholera toxin genes, to other vibrios.

By cholera toxin (CT) is meant the protein responsible for the clinical symptoms of cholera when produced by the bacteria.

By CTXΦ-encoded toxin genes are meant, in addition to CT genes, zot and ace genes that encode for the "zonula occludens toxin" and for the accessory cholera enterotoxin, respectively. The activity of ZOT is responsible for the destruction of the tight junctions between basolateral membranes of the epithelial cells and ACE protein has an activity accessory to that of the cholera toxin.

The term well tolerated vaccine or well tolerated strain refers to such strain lacking the residual reactogenicity that characterize most of the of non-toxigenic strains of *V. cholerae*. In practical terms, it means that it is a strain safely enough to be used in communities without or with limited access to healthcare institutions without risks for the life of the vaccinees. It should be expected a rate of diarrhea in 8% or less of the vaccinees and the diarrhea is characterized in that it does not exceed 600 ml (grs), only 1% of the vaccinees or less could suffer from headache, which should be minor and of short duration (less than 6 h), and finally that it prompts vomits in less than 0.1% of the vaccinees, those vomits characterized for being a single episode of 500 ml or less.

By hemagglutinin protease (HA/P) is meant the protein secreted by *V. cholerae* manifesting dual function, being one of them the ability to agglutinate the erythrocytes of certain species and the other the property to degrade or to process proteins such as mucine and the cholera toxin.

By celA is meant the nucleotide sequence coding for the synthesis of the endoglucanase A. This protein naturally occurs in *Clostridium thermocellum* strains and has a β (1-4) glucan-glucano hidrolase activity able to degrade cellulose and its derivatives.

The term MSHA is referred to the structural fimbria of the surface of *V. cholerae* with capacity to agglutinate erythrocytes of different species and that is inhibited by mannose.

By reversion to virulence mediated by VGJΦ is meant the event in which a previously attenuated strain obtained by the suppression of CTXΦ genes reacquire all the genes of this phage through a mechanism completely dependent and mediated by VGJΦ and the interaction with its receptor, MSHA.

The possibility of disseminating the CTXΦ phage in a process mediated by VGJΦ is that in which the filamentous phage VGJΦ form a stable hybrid structure (HybPΦ) through genetic recombination with the DNA of CTXΦ and disseminate its genome with active genes toward other strains of *V. cholerae*, which could be environmental non pathogenic strains, vaccine strains or other from different species.

Second, information of the previous art:

Clinical cholera is an acute diarrheal disease that result from an oral infection with the bacterium *V. cholerae*. After more than 100 years of research in cholera there remains the need for an effective and safe vaccine against the illness. Since 1817 man has witnessed seven pandemics of cholera, the former six were caused by strains of the Classical biotype and the current seventh pandemic is characterized by the prevalence of strains belonging to El Tor biotype. Recently, beginning in January of 1991, this pandemic extended to South America, and caused more than 25 000 cases of cholera and over 2 000 deaths in Peru, Ecuador and Chile. By November 1992, a new serogroup of *V. cholerae* emerged in India and Bangladesh, the 0139, showing a great epidemic potential and generating great concern through the developing world. These recent experiences reinforce the need for effective cholera vaccines against the disease caused by *V. cholerae* of serogroups O1 (biotype El Tor) and O139.

Because convalescence to cholera is followed by an state of immunity lasting at least three years, much efforts in *Vibrio cholerae* vaccinology have been made to produce live attenuated cholera vaccines, that closely mimics the disease in its immunization properties after oral administration, but do not result reactogenic to the individuals ingesting them (diarrhea, vomiting, fever). Vaccines of this type involve deletion mutations of all toxin genes encoded by CTXΦ. For example, the suppression of the cholera toxin and other toxins genes encoded in the prophage CTXΦ is a compulsory genetic manipulation during the construction of a live vaccine candidate (see inventions of James B. Kaper, WO 91/18979 and John Mekalanos WO 9518633 of the years 1991 and 1995, respectively).

This kind of mutants have been proposed as one dose oral vaccines, and although substantially attenuated and able to generate a solid immune responses (Kaper J. B. and Levine M. Patentes U.S. Pat. Nos. 06,472,276 and 581,406). However, the main obstacle for the widespread use of those mutants has been the high level of adverse reactions they produce in vaccinees (Levine and cols., Infect. and Immun. Vol 56, No1, 1988).

Therefore, achieving enough degree of attenuation is the main problem to solve during the obtainment of live effective vaccines against cholera. There are at least three live vaccine candidates, which have shown acceptable levels of safety, i.e., enough degree of attenuation and strong immunogenic potential. They are *V. cholerae* CVD103HgR (Classical Biotype, serotype Inaba) (Richie E. and cols, Vaccine 18, (2000): 2399-2410.), *V. cholerae* Perú-15 (Biotype El Tor, serotype Inaba) (Cohen M., and cols. (2002) Infection and Immunity, Vol 70, Not. 4, pag 1965-1970) and *V. cholerae* 638 (Biotype El tor, serotype Ogawa) (Benítez J. A. and cols, (1999), Infection and Immunity. February; 67(2):539-45).

Strain CVD103HgR is the active antigenic component of a live oral vaccine against cholera licensed in several countries of the world, the strains Perú-15 and 638 are other two live vaccine candidates to be evaluated in field trials in a near future.

However, there is a second problem of importance to solve in those live attenuated vaccine candidates; one is the environmental safety, specially related with the possible reacquisition and dissemination of the cholera toxin genes by existent mechanisms of horizontal transfer of genetic information among bacteria. In accordance with this, the attenuated vaccine strains of *V. cholerae*, could potentially reacquire virulence genes out of the controlled conditions of the laboratory, in an infection event with CTXΦ phage (Waldor M. K. and J. J. Mekalanos, Science 272:1910-1914) coming from other vibrios and later on contribute to their dissemination. This process could become relevant during vaccination campaigns where people ingest thousands of millions of attenuated bacteria and keep shedding similar quantities in their stools during at least 5 days. Once in the environment, bacteria have the possibility of acquiring genetic material from other bacteria of the same or different species of the ecosystem. For these reasons, at present it is desirable to obtain vaccine candidates with certain characteristics that prevent or limit the acquisition and dissemination of CTXΦ, and especially of the genes coding for the cholera enterotoxin. As a consequence, this is the field of the present invention.

Bacterial viruses, known as bacteriophages, have an extraordinary potential for gene transfer between bacteria of the same or different species. That is the case of CTXΦ phage (Waldor M. K. and J. J. Mekalanos, 1996, Science 272:1910-1914,) in *V. cholerae*. CTXΦ the genes of carries the genes that encode cholera toxin in *V. cholerae* and enters to the bacteria through interaction with a type IV pili, termed TCP, from toxin co-regulated pilus. TCP is exposed on the external surface of the vibrios. In accordance with published results, under optimal laboratory conditions the CTXΦ phage reaches titers of $10^6$ particles or less by ml of culture in the saturation phase; this allows classifying it as a moderately prolific bacteriophage. Equally the expression of the TCP receptor of this phage has restrictive conditions for its production. In spite of these limitations, the existence of this couple bacteriophage-receptor, limits in some way the best acceptance of live cholera vaccines, that is why depriving the bacteria from the portal of entrance to this phage is a desirable modification.

There are two theoretical ways of preventing the entrance of CTXΦ into *V. cholerae,* 1) suppressing the expression of TCP or 2) removing the TCP sites involved in phage receptor interaction. None of the two forms has been implemented due to the essentiality of TCP for proper colonization of the human intestine and elicitation of a protective immune response. It should be noted that sites involved in the TCP-CTXΦ interaction are also needed for the colonization process. (Taylor R. 2000. Molecular Microbiology, Vol (4), 896-910).

Several strategies that counteract the entrance of the virus have been evaluated such as preventing the integration of the phage to the bacterial chromosome and its stable inheritance, consisting in the suppression of the integration site and in the inactivation of recA gene to avoid recombination and integration to other sites of the chromosome. (Kenner and cols. 1995. J. Infect. Dis. 172:1126-1129).

Also, it has been recently described that the entry of CTXΦ into *V. cholerae* depends on the genes TolQRA, however this mutation produces sensitive phenotypes not undesired in vaccine candidates of cholera and it has not been implemented. (Heilpern and Waldor. 2000. J. Bact. 182:1739).

Further methods that prevent the entrance of phages carryings essential virulence determinants to cholera vaccine strains or other vaccine strains have not been described.

SUMMARY OF THE PRESENT INVENTION

The main subject of the present invention is related with the phage VGJΦ and its capacity to transfer the genes coding for the cholera toxin, using the Mannose Sensitive Hemagglutinin (MSHA) fimbria as receptor. Specifically, it consists in protecting the live attenuated vaccine strains from the infection with VGJΦ by introducing suppression mutations or modifications that prevent the correct functioning of this fimbria.

In the previous knowledge of this fimbria, the following aspects can be summarized. The gene product of mshA was originally described to be the major subunit of a fimbrial appendage in the surface in *V. cholerae* that had the capacity to agglutinate erythrocytes of different species, this capacity being inhibited by mannose (Jonson G. and cols (1991). Microbial Pathogenesis 11:433-441). As such, the MSHA was considered a virulence factor of the bacteria (Jonson G. and cols (1994). Molecular Microbiology 13:109-118). In accordance with the attributed importance, mutants deficient in the expression of the MSHA were obtained to study its possible role in virulence. It was demonstrated that MSHA, contrary to TCP, is not required for colonization of the human small intestine by the El Tor and O139 *V. cholerae* (Thelin KH and Taylor RK (1996). Infection and Immunity 64:2853-2856). The MSHA has been also described as the receptor of the bacteriophage 493 (Jouravleva E. and cols (1998). Infection and Immunity, Vol 66, Not 6, pag 2535-2539), suggesting that this phage could be involved in the emergence of the O139 vibrios (Jouravleva E. and cols, (1998). Microbiology 144:315-324). Later on it has been described that the fimbria MSHA has a role in biofilm formation on biotic and a-biotic surfaces contributing thus to bacterial survival outside of the laboratory and the host (Chiavelli D. A. and cols, (2001). Appl. Environ Microbiol. July; 67(7):3220-25 and Watnick P. I. and Kolter R. (1999). Mol. Microbiol. November, 34(3): 586-95). It is evident from the previous data that several investigations related with the MSHA fimbria have been done, but none of them defines this pili as the receptor of a phage able to transduce in a very efficient way the genes of the cholera toxin and not only these genes but the complete genome of CTXΦ, what could notably contribute to their dissemination. Additionally, although an extensive search has been made no inventions related with this fimbria have been found, either as virulence factor or as a phage receptor mediating dissemination of CTXΦ.

On the other hand, it is common practices among those who develop live cholera vaccines to provide them freeze-dried. Thus, these preparations of the live bacteria are ingested after the administration of an antacid solution that regulates the stomach pH and so the bacterial suspension continues toward the intestine without being damaged in the stomach and achieves colonization in the intestine.

Elaboration of freeze-dried vaccines improves preservation of strains, facilitates preparation of doses, allows a long-term storage, limits the risks of contamination and makes the commercialization and distribution easier, without the need of a cold chain, generally not available in under developing countries.

Although *Vibrio cholerae* is considered a very sensitive microorganism to the freeze-drying process, some additives are known to enhance strain survival. Thus, for preservation of the vaccine strain CVD103HgR Classical Inaba, the Center for vaccine Development, University of Maryland, United States, the Swiss Institute of Sera and Vaccines, from Berne (ISSVB), developed a formulation, see (Vaccine, 8, 577-580, 1990, S. J. Cryz Jr, M. M. Levine, J. B. Kaper, E. Fürer and B) that mainly contain sugars and amino acids. The formulation is composed of sucrose, amino acids and ascorbic acid, and after the freeze-drying process, lactose and aspartame are added.

In a work about preservation by freeze-drying of the wild type strain 569B Classical Inaba, published in Cryo-Letters, 16, 91-101 (1995) for Thin H., T. Moreira, L. Luis, H. García, T. K. Martino and A. Moreno, compared the effect of different additives on the viability and final appearance upon liophilization and after the storage at different temperatures of this *V. cholerae* strain. It was demonstrated that viability losses were less than 1 logarithmic order after 3 days of storage to 45° C.

The invention CU 22 847 claims a liophilization method where the formulations contain a combination of purified proteins or skim milk with addition of polymers and/or glycine, besides bacteriologic peptone or casein hydrolysate and sorbitol, with good results for the viability of *Vibrio cholerae* strains of different serogroups, biotypes and serotypes. The freeze-dried bacteria keep their viability after being dissolved in a 1,33% sodium bicarbonate buffering solution used to regulate the pH of the stomach.

Any vaccine formulation of cholera that it is supposed to be used in under developing countries should have certain requisites such as posses a simple composition, be easy to prepare and manipulate, be easy to dissolve and have good appearance after dissolved. Besides, It would be also desirable not to require low storage temperatures and to tolerate high storage temperatures at least for short periods of time, as well as the incidental presence of oxygen and humidity in the container. Additionally, it is also necessary an adequate selection of the composition of the formulation that allows the preservation of *Vibrio cholerae* of different serogroups, biotypes and serotypes. Finally, it is also remarkable that a formulation free of bovine derivate ingredients allows us to be in agreement with the international regulatory authorities related to the use of bovine components due to the Bovine Spongiform Encephalopathy Syndrome.

DESCRIPTION OF THE INVENTION

Figure 1:
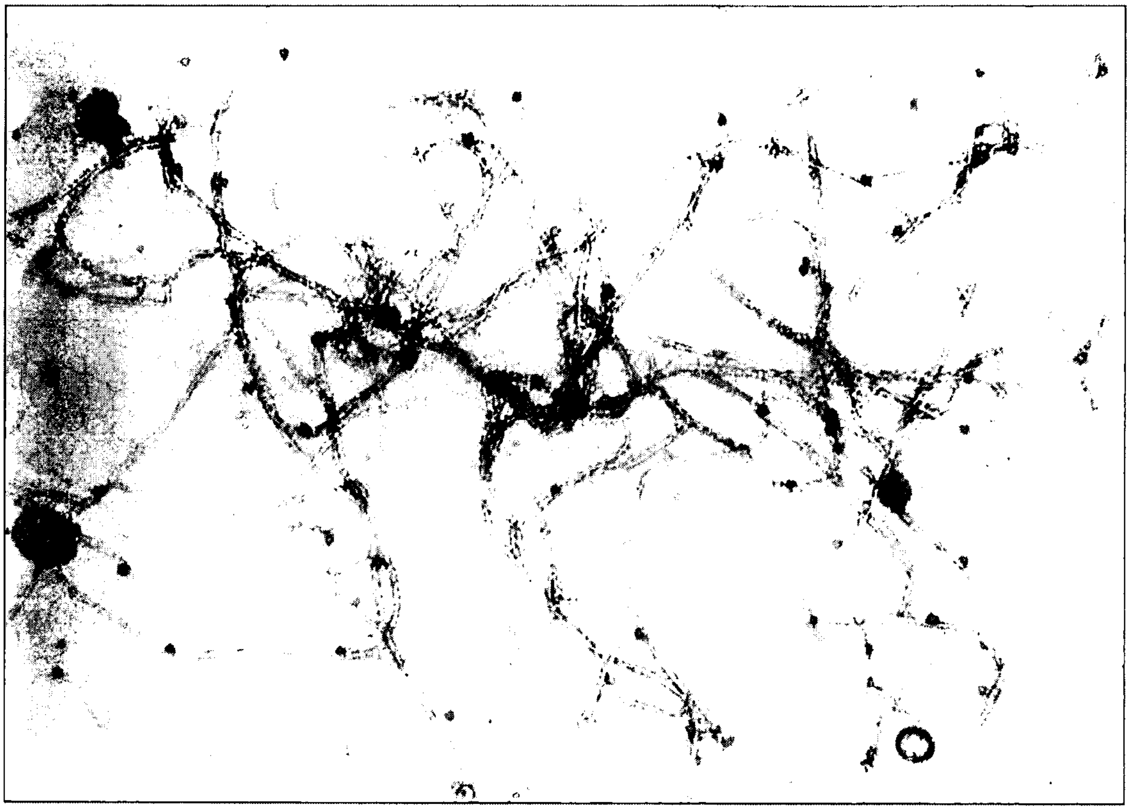
FIG. 1. Microphotography of VGJΦ phage. Magnification×32 000. VGJΦ phage was purified from the supernatants of infected *Vibrio cholerae* 569B.

The present invention propose a new generation of live attenuated vaccines to immunize against cholera by modification of their properties, specifically improving their biological safety during colonization of humans and later in the environment, outside the laboratories.

The present invention born from the necessity to protect live cholera vaccines from infection with the CTXΦ bacteriophage, which contains the cholera toxin genes, and also to impair the potential dissemination of this phage starting from live cholera vaccine candidates. Specifically it was born from the discovery and characterization of the VGJΦ phage in our laboratory.

VGJΦ is a filamentous bacteriophage isolated from *V. cholerae* O139 but it has infective capacity on *V. cholerae* O1 of all serotypes and biotypes and also over other strains of *V. cholerae* O139. The sequence of this phage was not described in the complete genome sequence of *V. cholerae*, indicating that this phage was not present in the strain N16961 (O1, El Tor Inaba). From a broad list of *V. cholerae* O1 strains existing in our laboratory, none of them had homologous sequences to VGJΦ, while strains MO45, SG25-1 and MDO12C, of *V. cholerae* O139 had.

The VGJΦ phage infects *V. cholerae* through the MSHA fimbria. When this phage enters to the bacterium it can replicate or integrate into a specific chromosomal region. This is a very active phage that reaches $10^{11}$ particles $ml^{-1}$ in the culture supernatants.

The most important characteristic in this phage, by virtue of which the following application of invention is issued, is their capacity to carry out a specialized transduction of the CTXΦ phage and consequently of the cholera toxin genes. This process occurs by a site-specific recombination between CTXΦ and VGJΦ genome, followed by the encapsulation and exportation of both genomes into the VGJΦ capsid. This hybrid viral particle was named HybPΦ. A culture of bacteria infected with both, CTXΦ and VGJΦ, produce $10^{11}$ particles $ml^{-1}$ of VGJΦ and $10^7$-$10^8$ particles $ml^{-1}$ of HybPΦ, which is at least 100 times higher than the titers obtained with CTXΦ alone.

It is also important to understand, to the purpose of this application that the CTXΦ phage receptor is TCP, which require special conditions for its expression, while the VGJΦ receptor is MSHA fimbria, an antigen that is expressed abundantly in all culture conditions studied and that is also produced in the environment. Furthermore, other vibrios produce the MSHA what increase the risk of transmission, even to other bacterial species.

It is also important to know that once, a new host become infected with HybPΦ, a stable production of particles in the range of $10^7$-$10^8$ $ml^{-1}$ takes place in the saturation phase, thus this hybrid phage has a high potential to transmit and disseminate the cholera toxin genes.

Another aspect of supreme interest to the purpose of this invention is that cholera toxin genes in HybPΦ are active enough to produce 50 ng $ml^{-1}$ of toxin during in vitro culture and that the infection of an attenuated strain with HybPΦ revert it back to virulence as assessed by the infant mouse cholera model.

In accordance with these data, a primary objective of the present invention is to describe the additional mutations made to live cholera vaccines to prevent them to be infected with either VGJΦ or HybPΦ, as well as the necessity to use live cholera vaccines from which the genome of VGJΦ is absent to avoid the dissemination of CTXΦ mediated by VGJΦ, in the case of reacquisition of CTXΦ.

An example of this mutation is a stable spontaneous mutation, conducive to the lack of expression of the MSHA fimbria in the cellular surface. This way, the VGJΦ or its derivative phage, HybPΦ could not infect such vaccines.

Another example of this mutation is a suppressive mutation in the structural gene of the major protein subunit of this fimbria (MshA).

The use of live cholera vaccine candidates in which the genome of VGJΦ is absent could be achieved simply by searching for hybridization of DNA in different strains to identify which have not homologous fragments to VGJΦ described in this invention, although other well known methodologies could be applied to remove VGJΦ from an infected strain.

Examples of live cholera vaccines to perform the specific mutations mentioned above are vaccine strains which are not able to react with a VGJΦ specific prove and that have been demonstrated in the previous art, to have acceptable levels of reactogenicity in volunteers studies. The genotype of these strains includes suppressive mutations of CTXΦ phage leaving a remnant RS1 and the insertional inactivation of hap gene with the celA gene. Such strains are constructed by means of traditional methods of suppression of the CTXΦ prophage in epidemics strains of *V. cholerae*, followed by the inactivation of the hemagglutinin protease gene (hap) for the insert of the marker gene celA in their sequence. To see Robert's scientific article and cols., Vaccine, vol 14 No16, 1517-22, 1996), the scientific article of Benítez J. A. and cols, (1999), Infection and Immunity. February; 67(2): 539-45, and the application of invention WO9935271A3, of Campos and cols, 1997. Other strains with these characteristic and that additionally have auxotrophy mutations are also useful to obtain the strains with the characteristics of interest of the present invention.

In accordance with the description in the above paragraph, a primary objective of this invention is to protect the use of suppressive or spontaneous mutations conductive to the absence of the MSHA fimbria in the surface of vibrios and in this way impede that live cholera vaccine reacquire and disseminate the cholera toxin genes by means of the infection with the hybrid phage, HybPΦ.

Among the preferred inclusions of this invention are any live cholera vaccine strain of the existing biotypes and serotypes or any non toxigenic strain of another emergent serotypes with genetic manipulations that suppress the genome of the CTXΦ phage, inactivate the hap gene, combined with any other mutation, for example the introduction of some auxotrophies (to lysine or metionine) and that also have the characteristics proposed in the present invention.

Among the preferred inclusions are also the use of the well tolerated live cholera vaccines, improved by the impossibility of acquiring the CTXΦ in an event mediated for VGJΦ and for the absence of VGJΦ that diminish the risk of dispersion of CTXΦ, as a delivery system to present heterologous antigens to the mucosal immune system.

To obtain these mutants in the expression of the MSHA fimbria we have used several molecular biology techniques which are not object of protection of the present document.

The present invention also discloses the methods to preserve and lyophilizate these strains with the purpose of being able to prepare live vaccines that present a rapid and adequate reconstitution post lyophilization without affecting their viability when being reconstituted in a solution of sodium bicarbonate 1,33%.

It is also the object of the invention that by means of the adequate selection of components, the lyophilized formulations guarantee that live cholera vaccines does not decrease their viability less than 1 logarithmic order as consequence of the storage, independently of the serogroup, serotype or biotype or the mutations they have, even if they were lyophilized for separate or mixed as part of a same preparation.

Among the formulation components to be present are lactose (L), peptone (P), yeast extract (E) and sorbitol (S). The total concentration should not exceed the 10%.

EXAMPLE 1

Discovery and Characteristics of the VGJϕ Phage

VGJϕ was discovered as an extrachromosomal transmissible element in total DNA preparations from *Vibrio cholerae* SG25-1, an O139 strain isolated in Calcuta India, 1993 and kindly donated by professor Richard A. Finkelstein. Simple experiments showed the transmissibility of this element. Free-cell culture supernatants of the donor strain, carrying the element, was grown in standard condition like LB media (NaCl 10 g/l, triptone 10 g/l and yeast extract 5 g/l) and was able to transfer to a receptor strain that does not contain any extrachromosomal element, one genetic element of the same size and restriction map that the one was present in the donor strain. The property of transmission without the direct contact between donor-receptor is typical in phages.

Infection Assays:

Donor strains were grown until optical density to 600 nm equal 0.2. One aliquot from the culture was filtered through a 0.22 μm- pore-size filter to remove the bacteria. The sterility of the filtrate was confirmed by growing one aliquot in LB plates and incubating overnight at 37° C. After checking the lack of colony forming units, 100 μl of free-cell supernatants or serial dilutions were used to infect 20 μl of a fresh culture of the receptor strain. The mixture was incubated for 20 min at room temperature and spread in solid or liquid LB media at 37° C. overnight. The infection was confirmed by the presence of replicative form (FR) and single strand DNA (ssDNA) of VGJϕ in the infected vibrios.

Purification of VGJϕ Phage:

Purification of phage particles was done from 100 ml of the culture of 569B *Vibrio cholerae* strain (classic, Inaba) infected with VGJϕ. This strain was used because it contains a CTXϕ defective prophage. The cells were centrifuged at 8000×g for 10 min. The supernatant was filtered through a 0.22 μm membrane. Phage particles in the filtrate were precipitated by addition of NaCl and polyethylene glycol 6000 to a final concentration of 3 and 5% respectively. The mixture was incubated in ice for 30 min and centrifuged at 12000×g for 20 min. The supernatant was discarded, and the phage-containing pellet was suspended in 1 ml of phosphate buffered saline.

Characterization of VGJϕ:

VGJϕ particles precipitated retained the capacity to infect 569B strain and were stable in PBS solution during at least 6 month at 4° C.

After phage particles purification, the genomic DNA was extract using phenol-chloroform solution. The analysis of this DNA showed resistance to digestion with ribonuclease H indicating that the genome is DNA and not RNA (data not shown) and it was also resistant to the treatment with different restriction enzyme but sensitive to treatment with Mung-Bean and Sl nuclease (data not shown), indicating that the phage genome consists of ssDNA. An electrophoresis analysis in the presence of acrydine orange demonstrated similar results to the previous ones. The acrydine orange intercalated in the double stranded DNA (dsDNA) fluoresce green, while fluoresce orange when intercalates in the ssDNA. As expected, the genomic DNA fluoresced orange indicating its single stranded nature (data not shown) and the plasmid DNA observed in the infected cells fluoresced green indicating that it consists of dsDNA.

Identity Between the Genome of VGJϕ and the Intracellular Replicative Form.

Southern blotting analysis carried out using the genome of VGJϕ as a probe showed a genetic identity between the extra-chromosomal elements of the donor strain SG25-1 and the infected strain 569B. This result confirms that the ssDNA of the viral genome is produced by the cytoplasmic RF and at the same time suggests that VGJϕ is a filamentous phage, which uses the rolling circle mechanism of replication to produce the genomic ssDNA that is assembled and exported in phage particles.

The RF, isolated from the infected strain 569B, was mapped by restriction analysis. The map obtained showed that the phage genome size (about 7500 b) and the electrophoretic restriction pattern were different to those of the previously reported *V. cholerae*-specific filamentous phages. These results indicated that the phage isolated from SG25-1 was not described previously and it was designated VGJϕ.

Titration of VGJϕ.

For tittering the phage suspensions the procedure was the same as the infection assay, but the indicator strain cells were plated onto an overlay of soft agar (0,4%) over solid LB plates. The plates were incubated overnight at 37° C. and the observed opaque plaques (infection focuses) were counted.

This assay revealed that a culture of 569B infected with VGJϕ is able to produce until $3\times10^{11}$ phage particles per ml of culture, what is unusually high compared with other described filamentous phages of *V. cholerae* like CTXϕ, which produces a maximum of $10^6$ particles per ml.

Electron Microscopy.

Different quantities of VGJϕ particles were negatively stained with a solution of 4% uranile acetate (m/v) and observed over a freshly prepared Formvar grids in a transmission electron microscope JEM 200EX (JEOL, Japan). The observation confirmed that the phage particles had a filamentous shape (FIG. 1).

Construction and Titration of VGJ-Knϕ.

The RF of VGJϕ was linearized by its unique XbaI site. One DNA fragment containing the R6K replication origin and a kanamycin resistance cassette from pUC4K plasmid was inserted in the XbaI site of VGJϕ. This recombinant RF was introduced in *V. cholerae* 569B and the phage particles were designated as VGJ-Knϕ.

The donor strain, 569B infected with VGJ-Knϕ, was cultured until an $OD_{600}$=2.0. An aliquot of the culture was filtered through a 0.2 um-pore-size filter to eliminate the bacterial cells. The sterility of the cell-free suspension was checked by plating an aliquot of 50 ul in a solid LB plate and incubating overnight at 37° C. Aliquots of 100 ul of the cell-free phage suspension or dilutions of it were used to infect 20 ul of a fresh culture of the receptor strain (about $10^8$ cells). The mixture was incubated at RT for 20 min to allow infection. Subsequently, the mixtures were plated onto solid LB supplemented with kanamycin (50 ug/ml) and the plates were incubated overnight at 37° C. The colonies that grow in the presence of antibiotic acquired their Kn-resistance due to the infection with the marked phage VGJ-Knϕ. Several of these colonies were checked for the presence of the RF of VGJ-knϕ by purification of plasmid DNA and restriction analysis of it.

Titration assay done by this method agreed with those obtained by that of opaque plaques with VGJϕ, showing that a culture of 569B infected by VGJ-knϕ produces about $2\times10^{11}$ particles of phage VGJ-knϕ per milliter of culture.

Nucleotide Sequence:

The nucleotide sequence of VGJϕ consisted of 7542 nucleotides and had a G+C content of 43.39%. The codified ORFs were identified and compared to protein data bases.

The genomic organization of VGJΦ was similar to that of previously characterized filamentous phage, such as phages of Ff group (M13, fd and f1) of *E. coli* and other filamentous phages of *V. cholerae* (CTXΦ, fs1, fs2 and VSK) and *V. parahemolyticus* (Vf12, Vf33 and VfO3k6). VGJΦ does not have a homologous gene to the gene IV of phages of Ff group which suggests that VGJΦ could use a porine of the host for assembling and exporting its phage particles, similar to CTXΦ phage.

The nucleotide sequence of VGJΦ revealed that VGJΦ is a close relative of fs1 and VSK phages, sharing several ORF highly homologous and exhibiting 82.8 and 77.8% of DNA homology to VSK and fs1. However, there are genome areas highly divergent and ORFs not share between them. Besides, the genome size is different and it has not been described before that fs1 or VSK being capable of transducing the genes of cholera toxin.

The nucleotide sequence of VGJΦ also revealed the presence of two sites homologous to att sequences known to function in integrative filamentous phage. These sites of VGJΦ are partially overlapped and in opposite directions. This arrangement was also found in phages Cf1c, Cf16-v1 and ΦLF of *X. campestris* as well as Vf33 and VfO3k6 of *V. parahemolyticus* and VSK of *V. cholerae*. All these phages except Vf33 and VSK integrate in the chromosome of their hosts by the att site present in the negative strand of the replicative form of these phages.

EXAMPLE 2

Identification of VGJΦ Receptor

Filamentous phages generally use type IV pili as receptor to infect their hosts. Previously reported *V. cholerae*-specific filamentous phages use TCP or MSHA pili as receptor. Therefore, two mutants of the El Tor strain C6706 for these pili, KHT52 (ΔtcpA10) and KHT46 (ΔmshA), were used to identify if any of them was the receptor of VGJΦ. While parenteral strain C6706 and its TCP-mutant KHT52 were sensitive to the infection with VGJΦ, the MSHA-mutant KHT46 was fully resistant to the phage, indicating that MSHA was the receptor of VGJΦ. Complementation of strain KHT46 with wild type mshA structural gene (from parental C6706) carried on plasmid pJM132 restored phage sensitivity, confirming that MSHA is the receptor for VGJΦ. The resistance or sensivity to VGJΦ was evaluated by the absence or presence of replicative form in cultures of receptor strain analyzed after the infection assay.

To give a numerical titer of the particles which are transduced in each case, it was used an infection assay with VGJΦ-kn as was described previously, resulting the following:

The parental strain C6706 and its derivative TCP mutant KHT52 were sensitive to the infection with VGJΦ-Kn and, as indicator strains showed titres of $10^{11}$ plaque forming units (PFU), while KHT46, a MSHA mutant, was fully resistant to the phage, less than 5 PFU/mL, after being infected with the same preparation of VGJΦ-Kn. Complementation of strain KHT46 with wild type msha structural gene, restored phage sensitivity. These results confirm that a mutation that prevents the expression of MSHA pilus confers resistance to the VJGΦ infection.

Further assays to compare the capacity of HybPΦ and CTXΦ to infect Clasical and El Tor strains were done, using their kanamycin resistant variants. See the results in Table 1.

As it has been previously described, CTXΦ-Kn phage was obtained through the insertion of a kanamycin resistance cassette from the plasmid pUC4K (Amersham Biosciences), in the unique restriction site, NotI, of the replicative form of CTXΦ.

The HypPΦ phage was obtained during an infection assay where cell free culture supernatant of 569b strain co-infected with CTXΦ-Kn and VGJΦ-Kn was used to infect the receptor strain KHT52. The cells of this strain carrying kanamycin resistance, originally carried by CTXΦ-Kn and provided to HybPΦ, were purified and, they continued producing HybPΦ viral particles to the supernatant.

To check the efficiency of infection of the hybrid phage in Classical and El Tor vibrios, suspensions of CTXΦ-Kn and VGJΦ-Kn of the same title (1-5×$10^{11}$ particles/mL) were used to infect the receptor strains 569B (Classical) and C7258 (El Tor). In both cases, the receptor strains were grown in optimal condition for TCP expression, the CTXΦ receptor. The assay was done as follows, 200 μL of pure phage preparation were mix with 20 μL (about $10^8$ cells) of a fresh culture of a receptor strain during 20 min at room temperature, plated on solid LB supplemented with kanamycin and incubated over nigh at room temperature.

The numbers of colonies carry the Kn-resistance gene in their genome is the result of phage infections and show the capacity of each phage to infect different strains in routine laboratory condition. Those results are exposed in Table 1.

TABLE 1

Titration of CTXϕ-Kn and hybrid (HybPΦ-Kn) phages in 569B and C7258.

| Phage | Kn$^r$ colony number of receptor strain 569B | C7258 |
|---|---|---|
| CTXϕ-Kn | 5.8 × $10^5$ | 0 |
| HybPΦ-kn | 1.5 × $10^5$ | 7.5 × $10^4$ |

As it is shown in Table 1 the hybrid phage transduces CT genes more efficiently than CTXΦ, the ordinary vehicle of these genes. These results point out the importance of the CTXΦ transmission mediated by VGJΦ among *Vibrio cholerae* strains and stressed its relevance considering the ubiquity of MSHA, the functional receptor in these bacterial strains.

EXAMPLE 3

Mobilization of CTXΦ, its Mechanism and Reversion to Virulence

Infection of *V. cholerae* O1 or O139 strains that carry an active CTXΦ phage with VGJΦ gives rise to the production of infective particles that bear the CTXΦ phage genome inserted in the genome of VGJΦ. These particles of hybrid phages have been designated HybPΦ. The HybPΦ titers were evaluated by means of the use of a hybrid phage, which carries a kanamycin marker (HybPΦ-Kn), employing different strains as indicators. The resultant titers are shown in Table 1.

Figure 2:
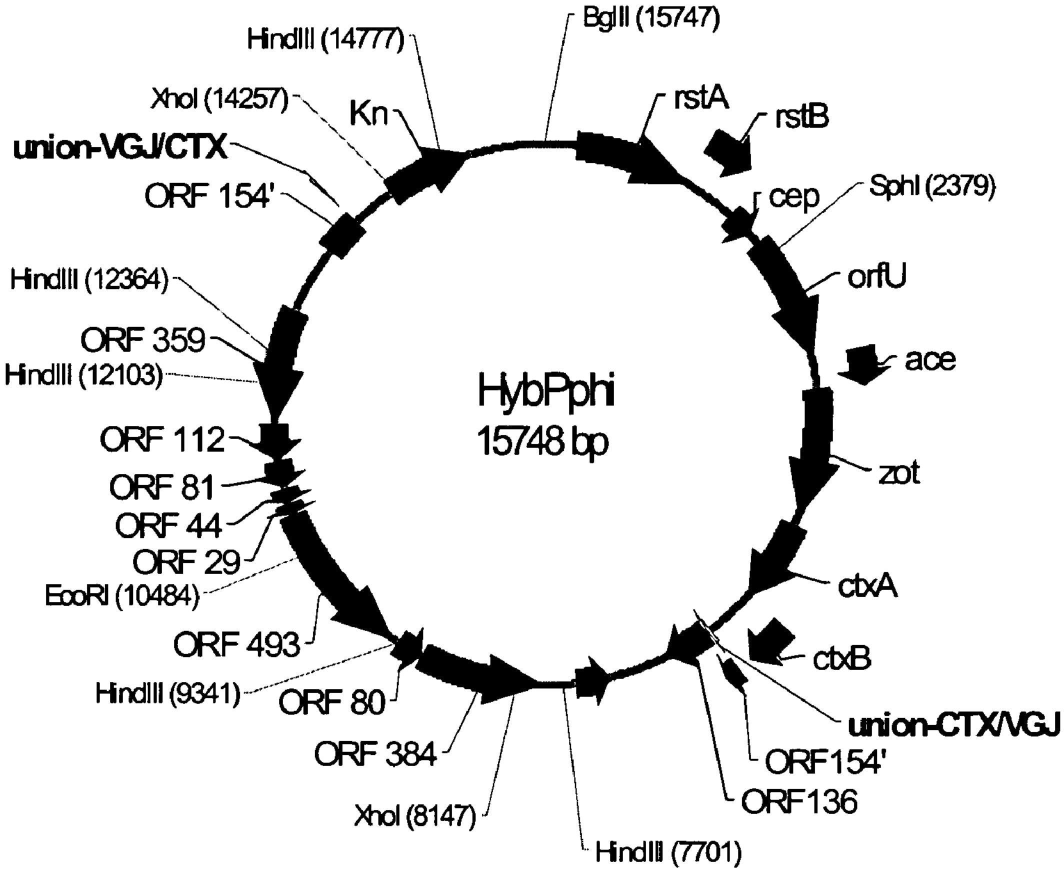
FIG. 2. Diagram of the genome of hybrid phage HybPΦ-Kn, which has a high potentiality for cholera toxin transmission. The att sequences shown are SEQ ID NO: 12-15.

HybPΦ-Kn was purified starting from preparations derived of 569B (HybPΦ-Kn) strain and the single strand was sequenced to determine the junctions between CTXΦ and VGJΦ. The cointegrate structure is graphically shown in the FIG. 2 and the nucleotide sequences of the junctions among both sequences, what explains the mechanism by which VGJΦ transduces CTXΦ toward other *V. cholerae* strains. HybPΦ-Kn enters to *V. cholerae* using the same receptor that VGJΦ, that is to say MSHA.

Figure 4:
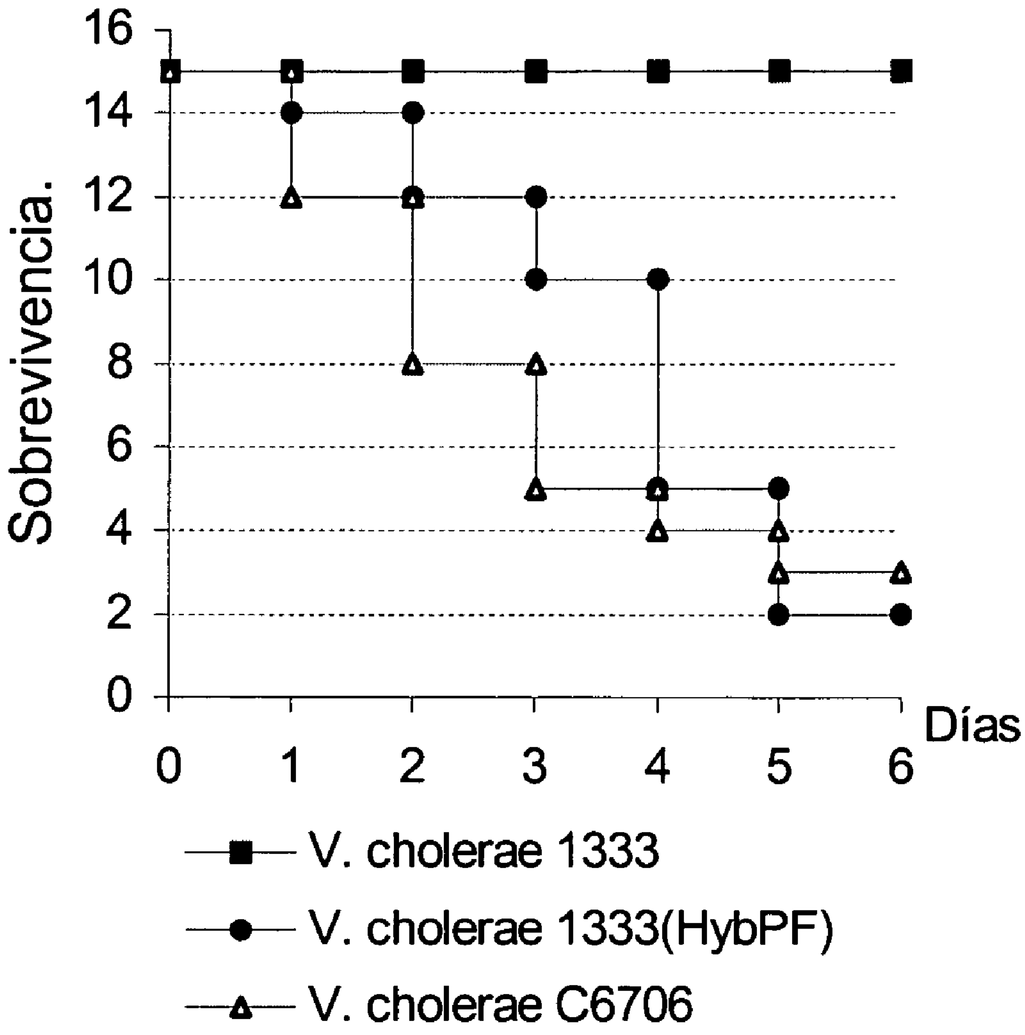
FIG. 4. Suckling Mice survival inoculated with an attenuated strain and its derivative infected with HybPΦ-Kn that revert it to virulence.

*V. cholerae* 1333 strain is an attenuated clone described in the previous art, similar to the strains that were useful for obtaining the derivative of the present invention. This strain is a derivative of the pathogenic C6706 strain. As it shows in the FIG. 4, the inoculation of $10^5$ colony-forming units of 1333 strain in suckling mouse does not have lethal effect, even when it is colonizing for the subsequent 15 days. Several experiments to determine virulence, demonstrated the effect of the HybPΦ-Kn infection on the reversion to virulence. While a dose of $10^5$ CFU of 1333 strain does not have a lethal effect, C6706 and 1333 (HybPΦ-Kn) strains have very similar lethality profiles, and don't allow survival of inoculated mouse beyond the fifth day (FIG. 4).

EXAMPLE 4

Constitutive Expression of the VGJΦ Receptor, the MSHA Fimbria, in Different Culture Conditions To study the expression of MshA, the major subunit of MSHA fimbria, *V. cholerae* C7258, C6706, and CA401 strains, were grown in different media. The media used were: LB pH 6.5 (NaCl, 10 g/l; bacteriological triptone, 10 g/l; yeast extract, 5 g/l), AKI (bacteriological peptone, 15 g/l; yeast extract, 4 g/l; NaCl, 0.5 g/l; NaHCO3, 3 g/l), TSB (pancreatic digestion of casein, 17 g/l; papaine digestion of soy seed, 3.0 g/l; NaCl, 5 g/l; dibasic phosphate of potassium, 2.5 g/l; glucose, 2.5 g/l), Dulbecco's (glucose, 4.5 g/l; HEPES, 25 mm; pyridoxine, HCl, HaHCO3), Protein Free Hybridoma Médium (synthetic formulation free of serum and proteins, suplemented with NaHCO3, 2.2 g/l; glutamine, 5 mg/l; red phenol, 20 g/l) and Syncase (NaH2PO4, 5 g/l; KH2PO4, 5 g/l; casaminoacids, 10 g/l; sucrose, 5 g/l and NH4Cl, 1.18 g/l). In all cases was inoculated one colony in 50 ml of culture broth and was grown in a rotary shaker during 16 hours at 37° C., with the exception of the AKI condition in which the strains were grown first at 30° C. in static form during 4 hours and later on rotator shaker at 37° C. during 16 hours. In each case, the bacterial biomass were harvested by centrifugation and used to prepare cellular lisates. Equivalent quantities of cellular lisates were analyzed by Western Blot with the monoclonal antibody 2F12F1 for immunodetection of mshA. The MSHA mutant strain KHT46 was used as negative control of the experiment. All the studied strains, except the KHT46 negative control strain, showed capacity to produce MshA in all culture conditions tested. Equally, said strains cultured in the previous conditions have the capacity to hemagglutinate chicken erythrocytes (mannose sensitive), in the same titer or higher to 1:16 and are efficiently infected by VGJΦ-Kn, exhibiting titers higher than $10^{10}$ particles per milliliter of culture.

EXAMPLE 5

Obtaining of Spontaneous Mutants Deficient in MSHA Expression and Evaluation of Resistance to Infection Strain KHT46, a MSHA suppression mutant, derived from *V. cholerae* C6706 (O1, The Tor, Inaba), shows a refractory state to the infection with VGJΦ, VGJΦ-Kn and the hybrid HybPΦ phages. However, this is a pathogenic strain that is not property of the authors of the present application, neither of the juridical person who presented it, The National Center for Scientific Research, in Havana City, Cuba.

To obtain the spontaneous mutants deficient in the expression of superficial MSHA of the present application, was used a suppression mutant in the cholera toxin genes that during the process of obtainment resulted affected in their capacity to assemble MSHA in the cellular surface. Said mutants although are capable of producing the structural subunit of MSHA, do not assemble it in their surface and therefore do not have detectable titers of mannose sensitive hemagglutination, neither adsorb the activity of a specific monoclonal antibody against the MSHA in a competition ELISA. Since this phenotype is notably stable, these mutants were subsequently genetically manipulated to introduce an insertional mutation in the hemagglutinin protease gene, following the procedure described in patent WO 99/35271 *"V. cholerae* vaccine candidates and the methods of their constructing" of Campos et al, and in the Robert's article, Vaccine, vol 14 No 16, 1517-22, 1996. The resultant mutants were named JCG01 and JCG02, both of O1 serogrup, El Tor biotype, Ogawa serotype.

JCG01 and JCG02 showed a refractory state to the infection with the VGJΦ-Kn phage, a variant of the VGJΦ phage that carries a resistance marker to kanamycin. A VGJΦ-Kn suspension that had a proven titer of ~$10^{11}$ units per ml, does not show capacity to infect said strains (non detectable titers, lower to 5 units for ml). This refractory state to the infection with VGJΦ-Kn correspond with a very low titer of hemagglutination in the strains JCG01 and JCG02 (1:2) regarding their parental (1:32) besides a total impairment in the MSHA dependent hemaglutination. Equally, whole cells of these mutants had null capacity to inhibit the interaction of the anti-MSHA monoclonal antibody (2F12F1) to MshA fixed on the solid phase in a competition ELISA. However, both strains produced the major structural subunit MshA, according to immunoblot experiments, indicating that the protein is not correctly assembling in the cellular surface although it is being produced. These mutants allowed proving the concept of this invention and passing to obtain suppression mutants.

Obtaining Suppression Mutants in the mshA Gene Starting from Other Cholera Vaccine Candidates.

To obtain suppression mutants in the mshA structural gene, two segments of the genome of *V. cholerae* N16961, of ~1200 base pairs for each flank of the mshA structural gene were amplified by means of the polimerase chain reaction, using the following oligonucleotides: CNC-8125, ATG ATC GTG AAG TCG ACT ATG (21 mer) (SEQ ID NO:2); CNC-8126 CAG CAA CCG AGA ATT HERE ATC ACC ACG (27 mer) (SEQ ID NO:3); CNC-8127, ATT CTC GGT TGC TGG AAC TGC TTG TG (26 mer) (SEQ ID NO:4); and CNC-8128, GCT CTA GAG TAT TCA CGG TAT TCG (24 mer) (SEQ ID NO:5). The amplified fragments were cloned independently and assembled in vitro to generate the pΔmshA clone. This clone contains these fragments in the same order and orientation that they are found in the bacterial chromosome; only the coding region of the mshA gene has been suppressed from the inner of the sequence. The fragment carrying the suppression was subcloned from the previous plasmid as a Sal I/Xba I fragment in the suicide vector pCVD442 to obtain the plasmid pSΔmshA.

Figure 3:
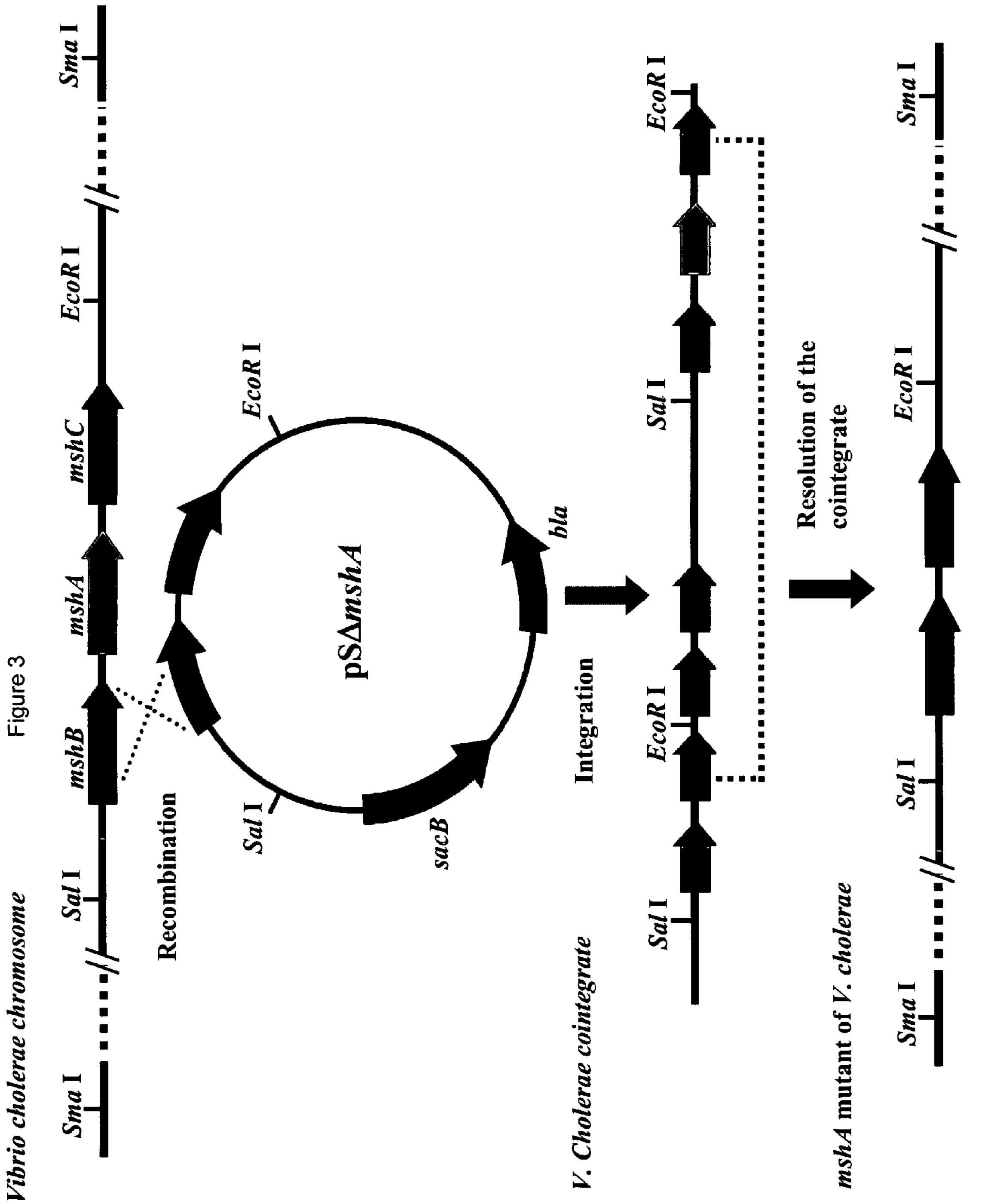
FIG. 3. Scheme of the genetic manipulation used to suppress mshA gene of *V. cholerae* vaccine candidates and the suicide vector used during the proceeding.

The plasmid pSΔmshA was used to suppress the chromosomal mshA gene in the *V. cholerae* vaccine strains by means of a traditional methodology of allelic replacement. For it, pSΔmshA was introduced in the *E. coli* strain SM10□pir and mobilized toward *V. cholerae* by means of a procedure of bacterial conjugation. The resultant clones were selected for their resistance to the ampicillin antibiotic in plates of LB medium supplemented with ampicillin (100 □g/ml) . Most of these clones arise due to integration of the plasmid in the chromosome of the receptor vibrios by means of an event of homologue recombination between one of the flanking fragments to the chromosome mshA gene and that of the plasmid pSΔmshA, originating a cointegrate between both. This event was verified by means of a Southern blot experiment, in which the total DNA of 10 clones was digested with the restriction enzyme Sma I and hybridized with a probe obtained from the plasmid pSΔmshA (Sal I/Xba I insert). The clones of our interest are those that produce a band of 21 000 base pairs. A similar control of the parental strain in this experiment produced a band of 13 000 base pairs. The adequate clones were conserved immediately in LB glycerol at −70° C. Then 3 of them were cultured in the absence of the antibiotic selective pressure to allow that an event of homologue recombination eliminated the genetic duplication existing. This can happen by means of suppression of the original genetic structure (intact mshA gene) and replacement by a mutated copy present in the plasmid (supressed mshA gene) as is shown in FIG. 3. The clones in which the mutated gene replaced the intact gene were analyzed by Southern blot and identified by the presence of a band of 12 000 base pairs. Finally, the clones where the mshA gene was suppressed were selected and conserved appropriately as vaccine candidates (freezing at −80° C. in LB supplemented with 20% glycerol). This procedure was performed with each clone where the mshA suppression mutant was constructed.

Serological Characterization

After the introduction of each mutation in the vaccine strains described in this document, each derivative was checked for the correct expression of the lipopolysaccharide corresponding to the original serotype. For that, cells were collected from a fresh plate, resuspended in saline (NaCl, 0.9%) and immediately examined with an appropriate agglutination serum, specific for Ogawa, Inaba or O139 vibrios.

The major immune response generated by an anti-cholera vaccine, is against the LPS, therefore the expression of the antigen corresponding to each one of the strains presented in this invention was confirmed by agglutination with specific antiserum.

Colonization Assay in Suckling Mice

The colonization assay in suckling mice (Herrington et al., J. Exper. Med. 168: 1487-1492, 1988) was used to determine the colonizing ability of each strain. An inoculum of $10^5$-$10^6$ vibrios in a volume of 50 □l was administered by orogastric route to groups of at least 5 suckling mice. After 18-24 hours at 30° C. the mice were sacrificed, the intestine was extracted and homogenized, and dilutions were plated in appropriate media for the growth of mutants.

TABLE 2

Colonizing capacity of the vaccine strains of the present invention.

| Strain | Inoculum | Colonizing | Genotype |
|---|---|---|---|
| BLR01 | $1.0 \times 10^5$ | $2.8 \times 10^4$ | ΔCTXΦ, hap::celA, ΔmshA |
| BLR02 | $2.0 \times 10^6$ | $4.2 \times 10^4$ | ΔVGJΦXΦ, hap::celA, lysA, |
| BLR03 | $1.2 \times 10^6$ | $8.0 \times 10^3$ | ΔCTXΦ, hap::celA, metF, |
| EMG01 | $3.0 \times 10^5$ | $8.0 \times 10^6$ | ΔCTXΦ, hap::celA, ΔmshA |
| EMG02 | $2.5 \times 10^5$ | $3.0 \times 10^6$ | ΔVGJΦXΦ, hap::celA, lysA, |
| EMG03 | $4.0 \times 10^5$ | $5.0 \times 10^5$ | ΔCTXΦ, hap::celA, metF, |
| JCG01 | $2.0 \times 10^5$ | $6.0 \times 10^6$ | ΔCTXΦ, hap::celA, $MSHA^-$ |
| JCG02 | $1.0 \times 10^5$ | $6.0 \times 10^7$ | ΔCTXΦ, hap::celA, $MSHA^-$ |
| JCG03 | $1.0 \times 10^5$ | $1.0 \times 10^6$ | ΔCTXΦ, hap::celA, ΔmshA |
| EVD01 | $3.0 \times 10^5$ | $3.0 \times 10^5$ | ΔVGJΦXΦ, hap::celA, thyA, |
| KMD01 | $1.0 \times 10^6$ | $7.0 \times 10^5$ | ΔCTXΦ, hap::celA, metF, |
| KMD02 | $2.0 \times 10^6$ | $5.0 \times 10^6$ | ΔCTXΦ, hap::celA, lysA, |
| ESP06 | $1.7 \times 10^6$ | $6.0 \times 10^5$ | ΔCTXΦ, hap::celA, ΔVC0934, |
| JCG04 | $1.0 \times 10^6$ | $2.0 \times 10^7$ | ΔCTXΦ, hap::celA, ΔmshA |
| ESP01 | $1.0 \times 10^5$ | $5.0 \times 10^6$ | ΔVGJΦXΦ, hap::celA, metF, |
| ESP02 | $6.0 \times 10^5$ | $4.0 \times 10^5$ | ΔCTXΦ, hap::celA, lysA, |
| ESP04 | $8.0 \times 10^4$ | $1.0 \times 10^6$ | ΔCTXΦ, hap::celA, ΔVC0934, |
| RAF01 | $3.1 \times 10^5$ | $5.0 \times 10^7$ | ΔCTXΦ, hap::celA, ΔmshA |
| EVD02 | $2.8 \times 10^5$ | $3.1 \times 10^6$ | ΔVGJΦXΦ, hap::celA, thyA, |
| ESP03 | $1.5 \times 10^5$ | $2.0 \times 10^6$ | ΔCTXΦ, hap::celA, metF, |
| KMD03 | $2.3 \times 10^5$ | $3.4 \times 10^6$ | ΔCTXΦ, hap::celA, lysA, |
| ESP05 | $2.1 \times 10^6$ | $2.3 \times 10^6$ | ΔCTXΦ, hap::celA, ΔVC0934, |
| TLP01 | $2.3 \times 10^6$ | $3.2 \times 10^5$ | ΔCTXΦ, hap::celA, ΔmshA |
| TLP02 | $3.4 \times 10^5$ | $9.4 \times 10^4$ | ΔVGJΦXΦ, hap::celA, lysA, |
| TLP03 | $2.7 \times 10^5$ | $8.8 \times 10^4$ | ΔCTXΦ, hap::celA, metF, |

All the strains showed adequate colonizing capacity to be used as live vaccine candidates. The colonization is needed to generate a strong immunological response because the local multiplication of the bacteria increases the duration of interaction with the mucosal immune system. In this case, although a perfect model for cholera does not exist, the suckling mice gives an adequate approach to what can be the subsequent colonization of each strain in humans.

Motility Assay

The cells of a well isolated colony are loaded in the tip of a platinum loop from a master plate toward a plate for the motility detection (LB, agar 0.4%), introducing the tip of the loop 2-3 mm in the agar. The diameter of dispersion of each colony in the soft agar to 30° C. is measured at 24 hours of incubation. A bacterial strain that reaches a diameter of 3 mm or less from the point of inoculation is considered as non-motile. A bacterial strain that grows in a diameter beyond 3 mm is considered as motile. All the strains included in this invention resulted to be motile.

EXAMPLE 6

Methods to Select and Construct the Vaccine Candidates Useful as Starting Strains to be Modified by the Procedure Disclosed in the Present Invention Five pathogenic strains in our collection were selected as starting microorganism due to their lack of hybridization with VGJΦ sequences. These strains are *V. cholerae* C7258 (O1, El Tor, Ogawa, Perú, 1991), C6706 (O1, El Tor, Inaba, Perú, 1991), CRC266 (O139, La India, 1999), CA385 (Clásico, Ogawa) y CA401 (Clásico, Inaba).

The procedures disclosed in this example are not the subject of the present invention. They rather constitute a detailed description of the methods used to obtain attenuated strains that are the substrate to construct the mutants claimed in the present invention. These mutants being characterized in that they are refractory to infection by VGJΦ and the hybrid VGJΦ::CTXΦ are obtained by the methods described in the examples 4 and 5.

Below we describe the suicide plasmids used to introduce different sets of mutations into *V. cholerae* by allelic replacement before they are suitable to be modified by the methods of the present invention. The reader should note that the strains claimed in the present invention have in addition to the mutation that impairs the correct expression of MSHA fimbriae (a) a deletion mutation of the cholera enterotoxin genes or the entire CTXΦ prophage and (b) the hemaglutinin protease gene interrupted with the *Clostridium thermocellum* endoglucanase A gene. They can also have additionally and optionally mutations in the genes (c) lysA, (d) metF, (e) VC0934 (coding for a glycosil transferase) and (f) thyA.

(a) To construct atoxigenic strains by inactivation of the cholera enterotoxin genes or deletion of the CTXΦ prophage, the suicide plasmid used was pJAF (Benitez y cols, 1996, Archives of Medical Research, Vol 27, No 3, pp. 275-283). This plasmid was obtained from plasmid pBB6 (Baudry y cols, 1991, Infection and Immunity 60:428), which contains a 5,1 kb insert from *V. cholerae* 569B that encodes ace, zot, ctxA y ctxB. Due to the absence of RS1 sequences 3' to the ctxAB operon in Classical vibrios, the EcoR I site downstream to the ctxAB copy in this plasmid lies in the flanking DNA of undefined function. The plasmid pBB6 was modified by deletion of the ScaI internal fragment to create plasmid pBSCT5, which now contains a recombinant region deprived of the zot and ctxA functional genes. Then the PstI of pBSCT5 was mutated into EcoRI by insertion of an EcoRI linker to obtain pBSCT64 and the resultant EcoRI fragment was subcloned into the EcoRI site of pGP704 to obtain pAJF.

(b) To construct strains affected in the expression of HA/P the suicide plasmid pGPH6 was used. This plasmid was constructed in different steps. First, plasmid pCH2 (Hase y Finkelstein, 1991, J. Bacteriology 173:3311-3317) that contains the hap gene in a 3,2 kb HindIII fragment from *V. cholerae* 3083 was linealized by the StuI site, which is situated in the hap coding sequence. The 3.2 kb HindIII-fragment containing the celA gene was excised from plasmid pCT104 (Cornet y cols, 1983, Biotechnology 1:589-594) and subcloned into the StuI site of pCH2 to obtain pAHC3. The insert containing of pAHC3, containing the hap gene insertionally inactivated with the celA gene, was subcloned as a HindIII fragment to a pUC19 derivative that have the multiple cloning site flanked by BglII sites to obtain pIJHCI. The Bgl II fragment of this plasmid was subcloned into pGP704 to originate pGPH6, which contains a 6.4 kb fragment with the genetic hap::celA structure, where the hap gene is not functional.

(c) y (d) When constructing mutants in the lysA or metF genes, the suicide plasmids pCVlysAΔ1 or pCVMΔClaI were used. To construct these plasmids, the lysA y metF genes were PCR amplified from *V. cholerae* C7258, using a pair of oligonucleotides for each gene. The oligonucleotides were purchased from Centro de Ingeniería Génetica y Biotecnología, Ciudad de La Habana, Cuba. The nucleotide sequences of the primers were: (lysA): (P 6488) 5'-GTA AAT CAC GCT ACT AAG-3' (SEQ ID NO:11) and (P 6487) 5'-AGA AAA ATG GAA ATGC-3'(SEQ ID NO:10) and (metF): (P 5872) 5'-AGA GCA TGC GGC ATG GC-3'(SEQ ID NO:8) and (P 5873) 5'-ATA CTG CAG CTC GTC GAA ATG GCG-3'(SEQ ID NO:9). The amplicons were cloned into the plasmids pGEM®T (Promega) and pIJ2925 (Janssen y cols, 1993, Gene 124:133-134), leading to the obtainment of the recombinant plasmids pGlysA3 y pMF29, which contain active copies of the lysA y metF genes, respectively. The identity of each gene was checked by nucleotide sequencing.

The metF and lysA genes cloned were mutated in vitro by deletion of the respective ClaI (246 base pairs) and PstI/AccI (106 base pairs) inner fragments, respectively. In the last of the cases the strategy was designed to keep the open reading frame leading to an inactive gene product to avoid exerting polar effects during and after construction of a lysA mutant of *V. cholerae*. Each inactivated gen was cloned as a Bgl II fragment in the suicide vector pCVD442 for the subsequent introduction into the cholera vaccine candidates of interest. The suicide plasmid containing the lysA alelle was termed pCVlysAΔ1 and the one containing the metF alelle was denominated pCVMΔClaI.

(e) When constructing mutants of the VC0934 gene we constructed and used the suicide plasmid pCVDΔ34. In doing that, the VC0934 gene was PCR amplified using as template total DNA from strain N16961 and the primers: 5'-GCA TGC GTC TAG TGA TGA AGG-3'(SEQ ID NO:6) and 5'-TCT AGA CTG TCT TAA TAC GC-3' (SEQ ID NO:7) The amplicon was cloned into the plasmid pGEM5Zf T-vector to obtain plasmid pGEM34; a 270 base pair deletion was performed inside the VC0934 coding sequence using the restriction enzymes NarI/BglII. After flushing the ends with klenow and subsequent recircularization the plasmid obtained was named pG34. The resultant inactive gene was subcloned into the suicide vector pCVD442 digested with SalI and SphI to obtain the plasmid pCVΔ34. This plasmid was used to make the allelic replacement of the wild type gene.

(f) When constructing mutants defective in thyA expression the suicide plasmid pEST was constructed and used. The steps to construct this plasmid comprised the cloning of the thyA gene from *V. cholerae* C7258 into pBR322 as an EcoRI-HindIII cromosomal DNA fragment, to obtain pVT1 (Valle y cols, 2000, Infection and Immunity 68, No 11, pp6411-6418). A 300 base pairs internal fragment from the thyA gene, comprised between the BglII and MluI, sites was deleted from this plasmid to obtain pVMT1. This deletion removed the DNA fragment that codes for amino acids 7 to 105 of the encoded protein Thimidilate syntase. The mutated thyA gene was excised as an EcoRI-HindIII fragment, the extremes were blunted and then cloned into the SmaI site of pUC19 in the same orientation as the β-galactosidase gene to obtain pVT9. The resultant gene was subcloned as a SacI fragment from pVT9 to pCVD442 and the obtained plasmid was named pEST. This final construct was used to make the allelic replacement of the wild type gene in the strains of interest.

The described suicide vectors are a modular system that can be used to introduce secuencial mutation into *V. cholerae* vaccine candidates.

The allelic replacement with the genes encoded by these vectors is done following the sequence of steps denoted below:

In the first step the suicide vector, containing the allele of choice among those described, is transferred by conjugation from the *E. coli* donor SM10λpir to the *V. cholerae* recipient, this last being the subject of the planned modification. This event is done to produce a cointegrate resistant to ampicillin. The clones resultant from the conjugational event are thus selected in LB plates supplemented with ampicillin (100 μg/ml).

The procedure for this first stage is as follows. The donor strain, SM10λpir transformed with the sucide vector of interest, is grown in an LB plate (NaCl, 10 g/l; bacteriological triptone, 10 g/l, and yeast extract, 5 g/l), supplemented with ampicillin (100 zg/ml), and the receptor strain, the *V. cholerae* strain to be modified, is grown in an LB plate. The conditions for growth are 37° C. overnight. A single colony of the donor and one from the receptor is streaked into a new LB plate. The donor strain is streaked firstly in one direction and the receptor (*V. cholerae*) secondly in the opposed orientation. This perpendicular and superimposed streaking warrant that both strain grow in close contact. In the next step the plates are incubated at 37° C. for 12 hours, harvested in 5 ml of NaCl (0.9 %) y 200 μl of dilutions $10^2$, $10^3$, $10^4$ and $10^5$ are disseminated in LB-ampicillin-polimixinB plates, to select the *V. cholerae* clones that were transformed with the suicide plasmid and counterselect the donor *E. coli* SM10λpir. Ten such clones resulting from each process are preserved frozen at −80° C. in LB-glicerol at 20% to be analyzed in the second step.

In the second step, a Southern blot hybridization is performed with a probe specific for the gene subjected to the mutational process; this is done to detect the structure of the correct cointegrate among the clones conserved in the previous step. The clones in which the suicide plasmid integrated to the correct target by homologous recombination are identified by the presence of a particular cromosomal structure. This structure contains one copy of the wild type gene and one of the mutated allele separated only by plasmid vector sequences. This particular structure produces a specific hybridization pattern in Southern blot with the specific probe that allows its identification. The appropriate clones are conserved frozen at −80° C. in LB glicerol.

This second step comprises the following substeps: Firstly, the total DNA of each clone obtained in the first step is isolated according to a traditional procedure (Ausubel y cols, Short protocols in Molecular Biology, third edition, 1992, unit 2.4, page 2-11, basic protocol). Total DNA from the progenitor strain is isolated as control. Then, the total DNA of the ten clones the progenitor strain is digested with the appropriate restriction enzymes, to be mentioned subsequently in the document. One μg of DNA are digested from each clone and the mother strain and later electrophoresed in parallel lanes of an agarose gel. The DNA content of the gel is blotted into membranes in alkaline conditions (Ausubel y cols, Short protocols in Molecular Biology, third edition, 1992, unit 2.9 A, page 2-30, alternate protocol 1).

The blots are fixed by incubation at 80° C. for 15 minutes. The free sites in the membrane are then blocked by prehybridization and subsequently probed with the specific probe for each mutation.

What follows are the details of the restriction enzyme, the probe (digoxigenin-labelled using the method random primed method) and the size of the hibridization fragment that identify the desired structure for the cointegrate of each clone, according to the target gene:

For suppression mutants of the CTXΦ phage genes, the total DNA of clones is digested with the restriction enzyme Hind III, and once in the membrane is hybridized with a probe obtained starting from the Pst I-EcoR I fragment of the pBB6 plasmid. The clones of interest are the ones that have the genetic structure that origin two bands in the Southern blot, one of 10 000 base pairs and another of 7 000 base pairs. As control the parental strain origins a single band of 17 000 base pairs in the same experiment of Southern blot.

For suppression mutants of the hap gene, the total DNA of clones is digested with the restriction enzyme Xho I, and once in the membrane is hybridized with a probe obtained starting from the Hind III fragment of 3 200 base pairs presents in the pCH2 plasmid. The clones of interest are those that have the genetic structure that origins a single band in the Southern blot, of 16 000 base pairs. As control the parental strain generates a single band of 6 000 base pairs in the same experiment of Southern blot.

For suppression mutants of lysA gene, the total DNA of clones is digested with the restriction enzyme Xho I, and once in the membrane is hybridized with a probe obtained from the Sph I/Sma I fragment of the pCV□lysAl plasmid, contained the mutated gene lysA. The clones of interest are those that have the genetic structure that origins a single band in the Southern blot, of 12 500 base pairs. As control the parental strain generates a single band of 5 200 base pairs in the same experiment of Southern blot.

For suppression mutants of metF gene, the total DNA of clones is digested with the restriction enzyme Nco I, and once in the membrane is hybridized with a probe obtained from the Bgl II fragment of pCVM□ClaI, contained the mutated metF gene. The clones of interest are those that have the genetic structure that origins a single band in the Southern blot, of 12 000 base pairs. As control the parental strain generates a single band of 5 000 base pairs in the same experiment of Southern blot.

For suppression mutants of gene VC0934, the total DNA of clones is digested with the restriction enzyme Ava I, and once in the membrane is hybridized with a probe obtained from the Sal I/Sph I fragment of pCVD□34, contained the mutated VC0934 gene. The clones of interest are those that have the genetic structure that origins two bands in the Southern blot, one of 1 600 or 1 900 and another of 8 200 or 7 900 base pairs. As control the parental strain generates a single band of 3 500 base pairs in the same experiment of Southern.

For suppression mutants in thyA gene, the total DNA of clones is digested with the restriction enzyme Bstx I, and once in the membrane is hybridized with a probe obtained from the Sac I fragment of pEST1, contained the mutated thyA gene. The clones of interest are those that have the genetic structure that origins a single band in the Southern blot, of 9 600 base pairs. As control the parental strain generates a single band of 2 400 base pairs in the same experiment of Southern blot.

In the third step of the procedure, 3 clones of interest, carrying a cointegrate with one of the previous structures, are cultured in absence of the antibiotic selective pressure to allow the loss of the suicidal vector by means of homologue recombination and the amplification of resultants clones. In said clones the loss of the suicidal vector goes with the loss of one of the two copies of the gene, the mutated or the wild one, of the genetic endowment of the bacteria.

In a fourth step of the procedure, dilutions of the previous cultures are extended in plates to obtain isolated colonies, which are then replicated toward plates supplemented with ampicillin to evaluate which clones are sensitive to ampicillin. Said clones, sensitive to ampcillin, are conserved for freezing, as described previously.

In a fifth step, by means of a study of Southern blot with specific probes for each one of the genes of interest (describe in a, b, c, d, and, f) it is verified which clones retained in the chromosome the mutated copy of the allele of interest. These clones of interest are expanded to create a work bank and to carry out their later characterization, as well as the introduction of the modifications object of protection in the present invention application.

In the following paragraphs we detail the restriction enzyme, the probe and the sizes of the hybridization fragments that identify the desired structure in each of the mutants, according to each of the genes being the subject of modification:

To analyze the mutants in the CTXΦ prophage, the total DNA is digested with the restriction endonuclease Hind III. Once in the membrane it is hybridized with a probe derived from the Pst I-EcoR I fragment of plasmid pBB6. Are clones of interest such that do not produce hybridization bands in the Southern blot.

For the mutants with the inactivated allele of hap, total DNA from the clones is digested with the restriction enzyme Xho I and once in the membrane it is hybridized with a probe derived from the 3 200 base pair Hind III fragment from plasmid $pCH_2$ that codes for the hap gen. The clones of interest are those that produce a single band in the Southern blot, of about 9 000 nucleotide pairs.

For the mutants in the lysA gene total ADN is digested with the restriction enzyme Xho I, and once in the membrane it is hybridized with a probe derived from the Sph I/Sma I fragment isolated from the plasmid pCVΔlysA, that contain the lysA mutated gene. The clones of interest are those having the genetic structure that produce a single band in Southern blot of about de 5 000 pairs of nucleotides.

For the mutants with deletions in the metF gene, the total ADN of the clones is digested with the restriction enzyme Nco I, and once in the membrane it is hybridized with a probe derived from the Bgl II fragment contained in plasmid pCVMΔClaI, that contains the metF mutant gene. The clones of interest are those that have the genetic structure that leads to a single band of 4 700 base pairs in the Southern blot.

For the mutants in the VC0934 gene, total DNA of the clones is digested with the restriction enzyme Ava I, and the blots are hybridized with a probe obtained from the Sal I/Sph I fragment of pCVDΔ34, which contains the VC0934 mutant gene obtained in vitro. The clones of interest are those having the structure leading to a single band of 3 200 base pairs in the Southern blot.

For the mutants in the thyA gene, total DNA of the clones is digested with the restriction enzyme Bstx I, and the blots are hybridized with a probe obtained from the Sac I fragment of pEST1, which contain the thyA gene. The clones of interest are those that have the genetic structure leading to a single band in the Southern blot of about 2 100 base pairs.

EXAMPLE 7

Methods to Preserve Vaccine Strains by Means of Lyophilization

In following example microorganisms were cultured in LB broth at 37° C. with an orbital shaking 150 and 250 rpm until reaching the logarithmic phase. Cells were harvested by centrifugation 5000 and 8000 rpm at 4° C. during 10-20 minutes and then were mixed with the formulations that show good protection features of the microorganism, so that the cellular concentration was between $10^8$ and $10^9$ cells $ml^{-1}$. 2 ml were dispensed for each 10R type flask. The lyophilization cycle comprised a deep freezing of the material, a primary drying keeping each product between −30° C. and −39° C. for space of 8 to 12 hours and a secondary drying at temperatures between 18° C. and 25° C. for not more than 12 hours. The viability loss was defined as the logarithmic difference of the CFU/mL before and after the lyophilization or before and after the storage of the lyophilized material, which is always dissolved in a 1.33% sodium bicarbonate solution.

Formulation L+E+S

The BLR01, JCG03 and ESP05 strains were processed by the previously described lyophilization process in a formulation of the type L (5.0%), E (2.0%) and S (2.0%). The freezing was performed at −60° C. During the primary drying, the temperature of the product was kept at −32° C. for 10 hours and in the secondary drying the temperature was kept at 22° C. for 12 hours. The dissolution of the lyophilized material in a 1.33% sodium bicarbonate solution was instant. The viability loss calculated immediately after the dissolution, with regard to the concentration of live cells before the lyophilization resulted to be 0.30, 0.43, and 0.60 logarithmic orders for BLR01, JCG03 and ESP05, respectively.

Comparison of the L+P+S and L+E+S Formulations with that of Skim Milk+Peptone +Sorbitol The strain JCG03 was lyophilized using two formulations: the type L (6.0%), P (2.0%) and S (2.0%), and the other type L (5.5%), E (1.8%) and S (1.6%). This strain was also lyophilized in a formulation of 6.0% skim milk, 2.0% peptone and 2.0% sorbitol as a comparison formulation. The freezing was done at −60° C. During the primary drying, the temperature of the product was kept at −33° C. for 12 hours and in the secondary drying the temperature was kept at 20° C. for 14 hours. The dissolution of the lyophilized material in a 1.33% sodium bicarbonate solution was instant when the lyophilization process took place in the formulations of the type L+P+S or L+E+S and slightly slower when was lyophilized in the comparison formulation. The viability loss calculated immediately after the dissolution, with regard to the concentration of live cells before the lyophilization resulted to be 0.48, 0.52 and 0.55 logarithmic orders for the L+P+S, L+E+S and the comparison formulations, respectively, significantly similar.

Humidity and Oxygen Effects

The strain JCG03 lyophilized in the three formulations mentioned in the previous paragraph, was exposed immediately after being lyophilized to the simultaneous action of humidity and oxygen. This was achieved, confining the samples during 3 days at 25° C. in an atmosphere in sterile glass desiccators, under an 11% relative humidity (created by a saturated solution of lithium chloride). The viability loss in the L+P+S, L+E+S and comparison formulations resulted to be 1.61, 1.10 and 3.43 logarithmic orders, respectively, what shows that the formulations object of this invention guarantee a bigger protection to humidity and oxygen than the comparison formulation.

Effect of the Storage Temperature

The strains TLP01, JCG01 and ESP05 were lyophilized in a formulation of the type L (5.5%), E(2.0%) and S(2.0%). The freezing was done at −58° C. During the primary drying, the temperature of the product was kept at −30° C. for 12 hours and in the secondary drying the temperature was kept at 20° C. for 14 hours. The dissolution in a 1.33% sodium bicarbonate solution was instant. The viability loss calculated immediately after the dissolution, with regard to the concentration of live cells before the lyophilization resulted to be 0.43, 0.55 and 0.44 logarithmic orders in TLP01, JCG01 and ESP05, respectively. The lyophilized material was stored 1 year either at 8° C. or −20° C. The Table 3 shows the viability loss results obtained.

TABLE 3

Viability loss (1 year of storage).

| Strain | 8° C. | −20° C. |
|---|---|---|
| TLP01 | 1.07 | 0.64 |
| JCG01 | 1.02 | 0.59 |
| ESP05 | 0.91 | 0.55 |

EXAMPLE 8

Strains of the Present Invention and Their Characteristics

The strains of the present invention have been deposited on Dec. 11, 2003 in the Belgium Coordinated Collection of Microorganisms (BCCM), Laboratorium voor Microbiologie-Bacterienverzameling (LMG), Universiteit Gent, K. L. Ledeganckstraat 35, B-9000 Gent, Beigium:

| | | |
|---|---|---|
| *Vibrio cholerae* | JCG01 | (LMG P-22149) |
| *Vibrio cholerae* | JCG02 | (LMG P-22150) |
| *Vibrio cholerae* | JCG03 | (LMG P-22151) |
| *Vibrio cholerae* | KMD01 | (LMG P-22153) |
| *Vibrio cholerae* | KMD02 | (LMG P-22154) |
| *Vibrio cholerae* | KMD03 | (LMG P-22155) |
| *Vibrio cholerae* | JCG04 | (LMG P-22152) |
| *Vibrio cholerae* | ESP01 | (LMG P-22156) |
| *Vibrio cholerae* | ESP02 | (LMG P-22157) |
| *Vibrio cholerae* | ESP03 | (LMG P-22158) |
| *Vibrio cholerae* | RAF01 | (LMG P-22159) |
| *Vibrio cholerae* | TLP01 | (LMG P-22160) |
| *Vibrio cholerae* | TLP02 | (LMG P-22161) y |
| *Vibrio cholerae* | TLP03 | (LMG P-22162) |

They are described in Table 4.

TABLE 4

Vaccine strains of the present invention.

| Strain | Wild type parental strain | Biotype/ Serotype | Relevante Genotype. |
|---|---|---|---|
| BLR01 | CA385 | Classical/Og | ΔCTXΦ, hap::celA, ΔmshA |
| BLR02 | CA385 | Classical/Og | ΔCTXΦ, hap::celA, lysA, ΔmshA |
| BLR03 | CA385 | Classical/Og | ΔCTXΦ, hap::celA, metF, ΔmshA |
| EMG01 | CA401 | Classical/In | ΔCTXΦ, hap::celA, ΔmshA |
| EMG02 | CA401 | Classical/In | ΔCTXΦ, hap::celA, lysA, ΔmshA |
| EMG03 | CA401 | Classical/In | ΔCTXΦ, hap::celA, metF, ΔmshA |
| JCG01 | C7258 | El Tor/Ogawa | ΔCTXΦ, hap::celA, $MSHA^-$ |
| JCG02 | C7258 | El Tor/Ogawa | ΔCTXΦ, hap::celA, $MSHA^-$ |
| JCG03 | C7258 | El Tor/Ogawa | ΔCTXΦ, hap::celA, ΔmshA |
| EVD01 | C7258 | El Tor/Ogawa | ΔCTXΦ, hap::celA, thyA, ΔmshA |
| KMD01 | C7258 | El Tor/Ogawa | ΔCTXΦ, hap::celA, metF, ΔmshA |
| KMD02 | C7258 | El Tor/Ogawa | ΔCTXΦ, hap::celA, lysA, ΔmshA |
| ESP06 | C7258 | El Tor/Ogawa | ΔCTXΦ, hap::celA, ΔVC0934, |
| JCG04 | C7258 | El Tor/Ogawa | ΔCTXΦ, hap::celA, ΔmshA |
| ESP01 | C7258 | El Tor/Ogawa | ΔCTXΦ, hap::celA, metF, ΔmshA |
| ESP02 | C7258 | El Tor/Ogawa | ΔCTXΦ, hap::celA, lysA, ΔmshA |
| ESP04 | C7258 | El Tor/Ogawa | ΔCTXΦ, hap::celA, ΔVC0934, |
| RAF01 | C6706 | El Tor/Inaba | ΔCTXΦ, hap::celA, ΔmshA |
| EVD02 | C6706 | El Tor/Inaba | ΔCTXΦ, hap::celA, thyA, ΔmshA |
| ESP03 | C6706 | El Tor/Inaba | ΔCTXΦ, hap::celA, metF, ΔmshA |
| KMD03 | C6706 | El Tor/Inaba | ΔCTXΦ, hap::celA, lysA, ΔmshA |
| ESP05 | C6706 | El Tor/Inaba | ΔCTXΦ, hap::celA, ΔVC0934, |
| TLP01 | CRC266 | O139 | ΔCTXΦ, hap::celA, ΔmshA |
| TLP02 | CRC266 | O139 | ΔCTXΦ, hap::celA, lysA, ΔmshA |
| TLP03 | CRC266 | O139 | ΔCTXΦ, hap::celA, metF, ΔmshA |

Advantages

The present invention provide us with a methodology to protect live cholera vaccine candidates from the reacquisition of cholera toxin genes and others toxins from the CTXΦ bacteriophage mediated by VGJΦ phage, and therefore from the conversion to virulence by this mechanism.

Equally provide us with the necessary information to assure that live cholera vaccine candidates will not spread CTXΦ, in the case that these vaccine candidates reacquire CTXΦ, by a specialized transduction with the VGJΦ phage.

The present invention provide us the application of MSHA mutants as live cholera vaccine candidates, which exhibits an increase in their environmental safety due to resistance to the infection with CTXΦ mediated by VGJΦ.

This invention provides us with a new characteristic to keep in mind during the design and construction of live cholera vaccine candidates to improve their environmental safety, that is to say that such vaccines are not able to spread the CTXΦ genes, mediated by VGJΦ, in the case of reacquisition.

The above characteristic could be applied to the already made live cholera vaccine candidates, which have demonstrated an acceptable level of reactogenicity in volunteers studies, to reduce their potential environmental impact.

This invention also provide formulations to preserve by lyophilization all of the above-mentioned live cholera vaccine candidates and also improve their abilities to tolerate the remainder of oxygen and humidity in the container.

These formulations also guarantee the instant reconstitution of the lyophilized live cholera vaccine candidate powder in sodium bicarbonate buffer, making easier the manipulation, protecting the vaccines during this process and improving the organoleptic characteristic, specifically related with the visual aspect of lyophilized tablets and the reconstituted products.

One of the formulations provided here for conservation and lyophilization of live cholera vaccine candidates lack the bovine components usually added to many formulations to lyophilize human vaccines.

The invention claimed is:

1. A freeze-dried composition comprising one or more living attenuated strains of Vibrio cholerae, wherein the one or more strains of Vibrio cholerae comprise at least one mutation inactivating at least one gene essential for the biogenesis of mannose-sensitive hemagglutinin fimbria (MSHA), and further lack sequence of the VGJΦ phage (SEQ ID NO: 1), and the composition contains lactose sorbitol, and either peptone or yeast extract at a total concentration not higher than 10%.

2. The composition according to claim 1, wherein the freeze dried composition comprise one or more strains of Vibrio cholerae selected among those listed below which were deposited for patent purposes at the BCGM, LMG international depository authority under the terms of the Budapest Treaty:

Vibrio cholerae JCG01 (LMG P-22149);
Vibrio cholerae JCG02 (LMG P-22150);
Vibrio cholerae JCG03 (LMG P-22151), serogrupo O1, biotipo El Tor, serotipo Ogawa;
Vibrio cholerae KMD01 (LMG P-22153), serogrupo O1, biotipo El Tor, serotipo Ogawa;
Vibrio cholerae KMD02 (LMG P-22154), serogrupo O1, biotipo El Tor, serotipo Ogawa;
Vibrio cholerae KMD03 (LMG P-22155), serogrupo O1, biotipo El Tor, serotipo Inaba;
Vibrio cholerae JCG04 (LMG P-22152), serogrupo O1, biotipo El Tor, serotipo Ogawa;
Vibrio cholerae ESP01 (LMG P-22156), serogrupo O1, biotipo El Tor, serotipo Ogawa;
Vibrio cholerae ESP02 (LMG P-22157), serogrupo O1, biotipo El Tor, serotipo Ogawa;
Vibrio cholerae ESP03 (LMG P-22158), serogrupo O1, biotipo El Tor, serotipo Inaba;
Vibrio cholerae RAF01 (LMG P-22159), serogropa O1, biotipo El Tor, serotipo Inaba;
Vibrio cholerae TLP01 (LMG P-22160), serogrupo O139;
Vibrio cholerae TLP02 (LMG P-22161), serogrupo O139;
Vibrio cholerae TLP03 (LMG P-22162), serogrupo O139.

3. The composition according to claim 1 wherein the composition comprises lactose 6.0%; peptone 2.0% and sorbitol 2.0% or lactose 5.0%; yeast extract 2.0% and sorbitol, 2.0%.

* * * * *